(12) United States Patent
Regalado et al.

(10) Patent No.: US 11,554,189 B2
(45) Date of Patent: Jan. 17, 2023

(54) PLASMA TREATMENT DEVICE AND METHOD OF TREATING ITEMS

(71) Applicant: BLUEWAVE TECHNOLOGIES, INC., Orange City, FL (US)

(72) Inventors: Julius Regalado, Gainesville, FL (US); Xin Zhou, Gainesville, FL (US); Kenneth Cherisol, Lake Mary, FL (US); Miles Clark, Lake Helen, FL (US)

(73) Assignee: BLUEWAVE TECHNOLOGIES, INC., Orange City, FL (US)

( * ) Notice: Subject to any disclaimer, the term of this patent is extended or adjusted under 35 U.S.C. 154(b) by 270 days.

(21) Appl. No.: 17/074,664

(22) Filed: Oct. 20, 2020

(65) Prior Publication Data

US 2021/0030907 A1 Feb. 4, 2021

Related U.S. Application Data

(62) Division of application No. 15/537,961, filed as application No. PCT/US2015/067437 on Dec. 22, 2015, now Pat. No. 10,821,199.

(Continued)

(51) Int. Cl.
*A61L 2/14* (2006.01)
*A61L 2/10* (2006.01)
(Continued)

(52) U.S. Cl.
CPC ...... *A61L 2/14* (2013.01); *A61L 2/10* (2013.01); *A61L 2/22* (2013.01); *A61L 2/18* (2013.01);
(Continued)

(58) Field of Classification Search
CPC ..... A61L 2/10; A61L 2/14; A61L 2/18; A61L 2/22; A61L 2/186
See application file for complete search history.

(56) References Cited

U.S. PATENT DOCUMENTS 3,549,528 A 12/1970 Armstrong
3,554,687 A 1/1971 Cassidy
(Continued)

FOREIGN PATENT DOCUMENTS

EP 2275146 1/2011
JP 2003 159570 6/2003
(Continued)

OTHER PUBLICATIONS

Klämpfl, T.G. et al., "Cold Atmospheric Air Plasma Sterlization against Spores and Other Microorganisms of Clinical Interest," *Applied and Environmental Microbiology*, Aug. 2012, pp. 5077-5082, vol. 78, No. 15.
(Continued)

*Primary Examiner* — Sean E Conley
(74) *Attorney, Agent, or Firm* — Saliwanchik, Lloyd & Eisenschenk

(57) ABSTRACT

The use of plasma to clean or sterilize items can be particularly advantageous for items that cannot be readily washed or cleaned by standard methods. The toxicity and complications generating sufficient plasma makes it hard to use for such purposes. The subject invention addresses the problem by generating a minimal amount of highly reactive plasma to sterilize an item. This is achieved by reducing the amount of space and ambient air around and within the item. In this way, the plasma generated fills only the required volume of the item to be cleaned and the plasm is directed at the object, not directed at or released into non-target areas.

20 Claims, 22 Drawing Sheets

Related U.S. Application Data

(60) Provisional application No. 62/129,533, filed on Mar. 6, 2015, provisional application No. 62/095,629, filed on Dec. 22, 2014.

(51) Int. Cl.
  *A61L 2/22* (2006.01)
  *A61L 2/18* (2006.01)

(52) U.S. Cl.
  CPC ......... *A61L 2/186* (2013.01); *A61L 2202/122* (2013.01); *A61L 2202/14* (2013.01); *A61L 2202/16* (2013.01); *A61L 2202/26* (2013.01)

(56) References Cited

U.S. PATENT DOCUMENTS

| | | | |
|---|---|---|---|
| 3,719,017 A | 3/1973 | Shapiro et al. | |
| 5,520,893 A | 5/1996 | Kasting, Jr. et al. | |
| 6,312,645 B1 | 11/2001 | Lin et al. | |
| 10,821,199 B2 | 11/2020 | Regalado et al. | |
| 2002/0085950 A1 | 7/2002 | Robitaille et al. | |
| 2004/0005261 A1 | 1/2004 | Ko | |
| 2008/0118411 A1 | 5/2008 | D'Arinzo | |
| 2011/0081274 A1 | 4/2011 | Packman et al. | |
| 2014/0076712 A1 | 3/2014 | Jacob et al. | |

FOREIGN PATENT DOCUMENTS

| | | |
|---|---|---|
| JP | 2010187966 | 9/2010 |
| JP | 2012081215 | 4/2012 |
| WO | WO 2005/067984 | 7/2005 |
| WO | WO 2010/102000 | 9/2010 |

OTHER PUBLICATIONS

Machine translation for JP 2003159570, 2003, pp. 1-3.
Machine translation for JP 2010187966, 2010, pp. 1-12.

FIG. 3A
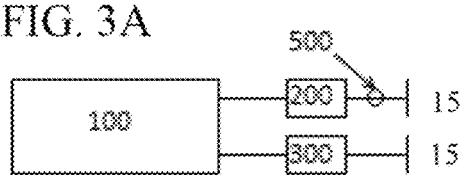
FIG. 3B
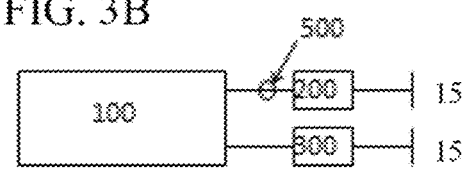
FIG. 4A
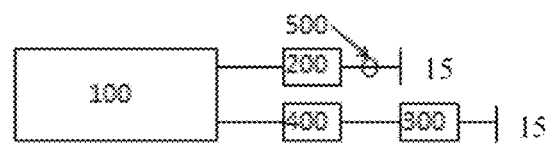
FIG. 4B
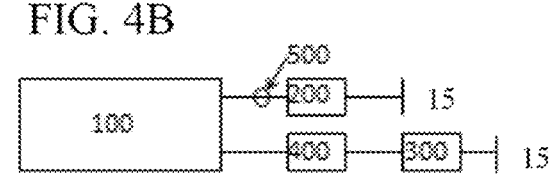
FIG. 4C
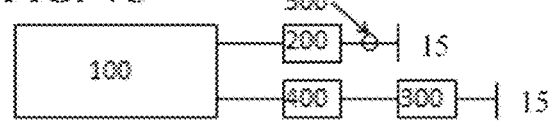
FIG. 4D
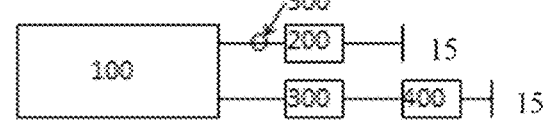
FIG. 4E
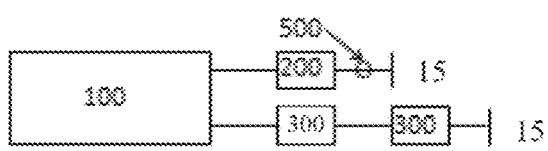
FIG. 5A
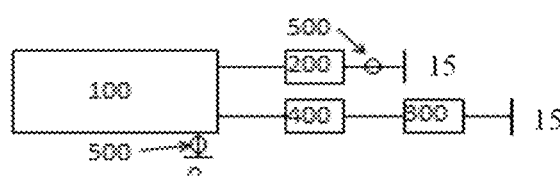
FIG. 5B
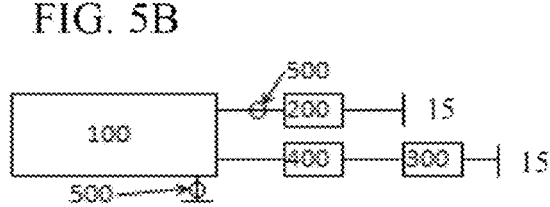
FIG. 5C
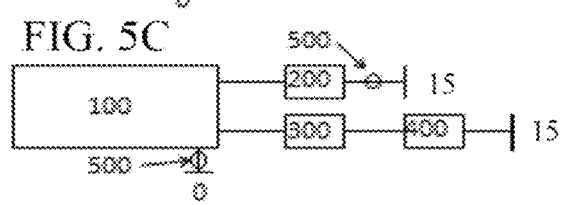
FIG. 5D
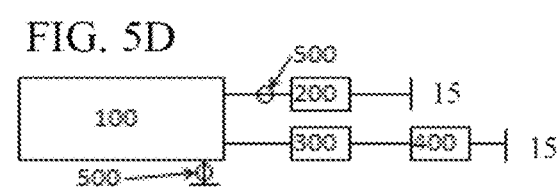
FIG. 6A
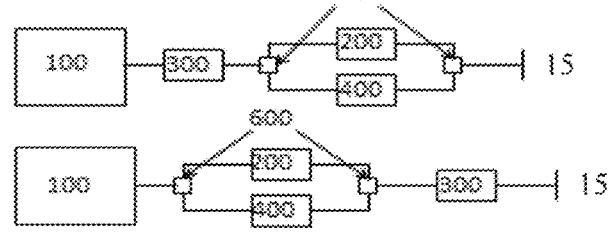
FIG. 6B FIG. 7A
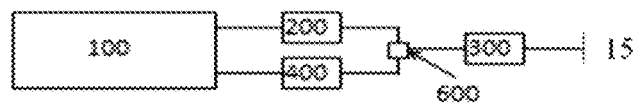
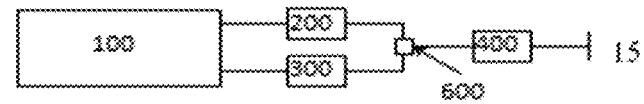
FIG. 7B
FIG. 8A
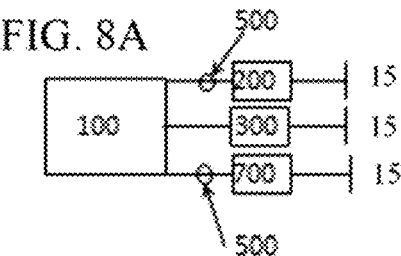
FIG. 8B
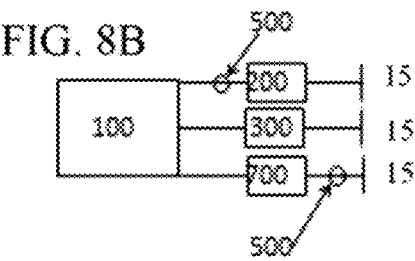
FIG. 8C
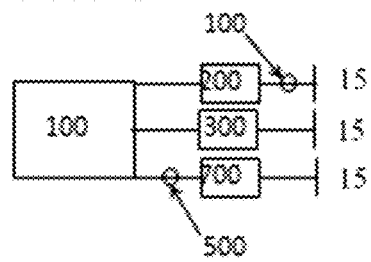
FIG. 8D
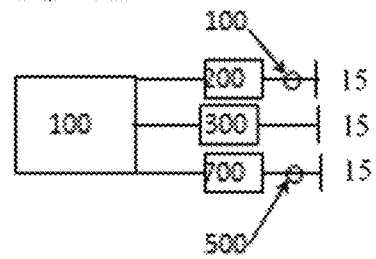
FIG. 9A 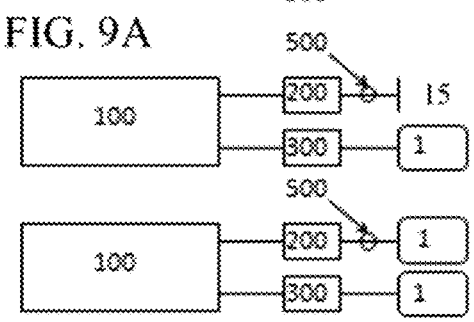 FIG. 9B 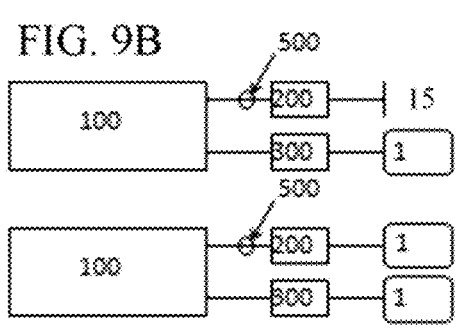
FIG. 9C
FIG. 9D
FIG. 9E 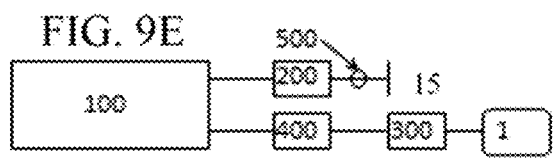 FIG. 9F 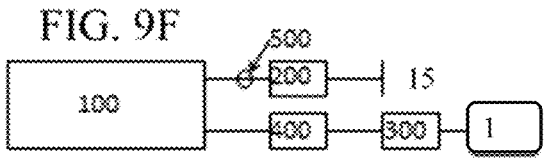
FIG. 9G 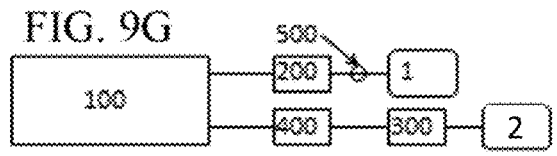 FIG. 9H 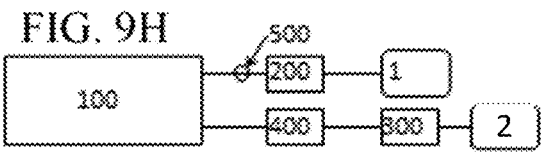

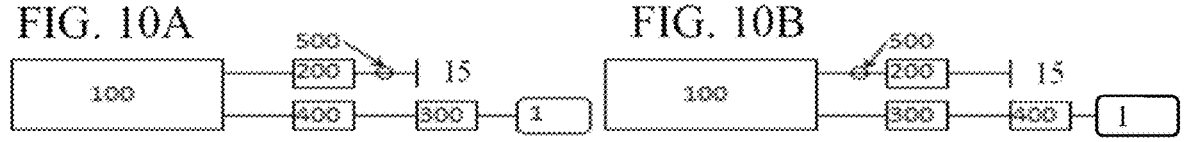
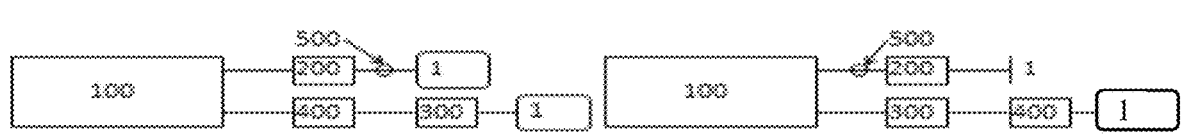
FIG. 10A  FIG. 10B
FIG. 10C  FIG. 10D
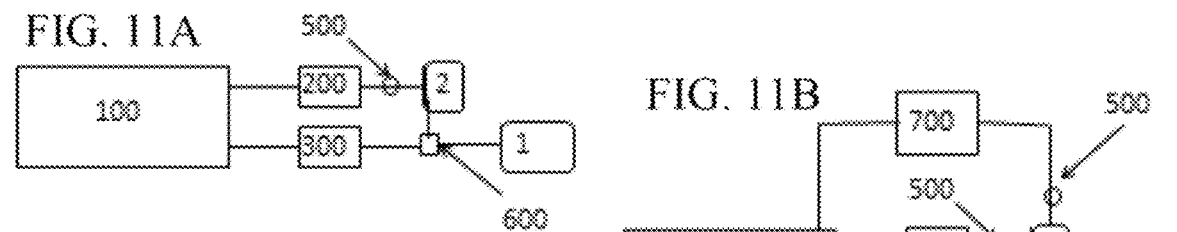
FIG. 11A
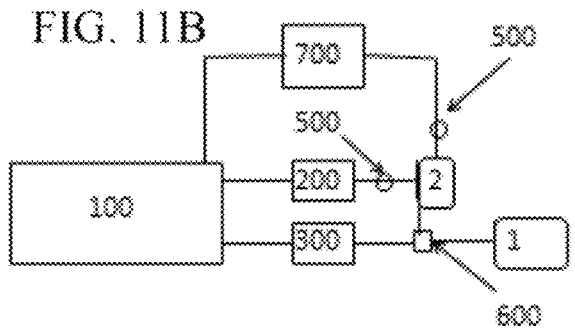
FIG. 11B
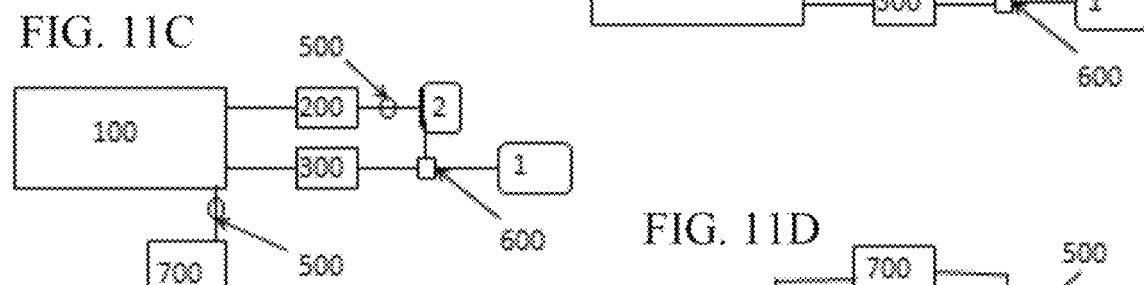
FIG. 11C
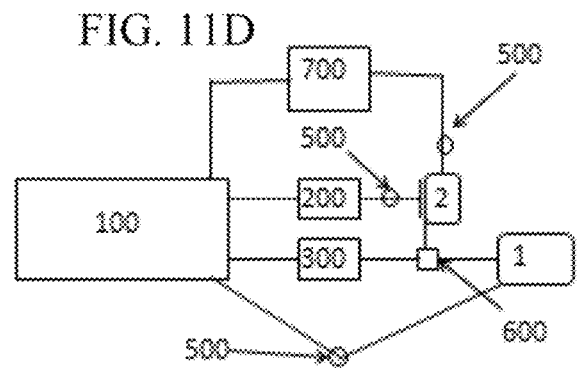
FIG. 11D

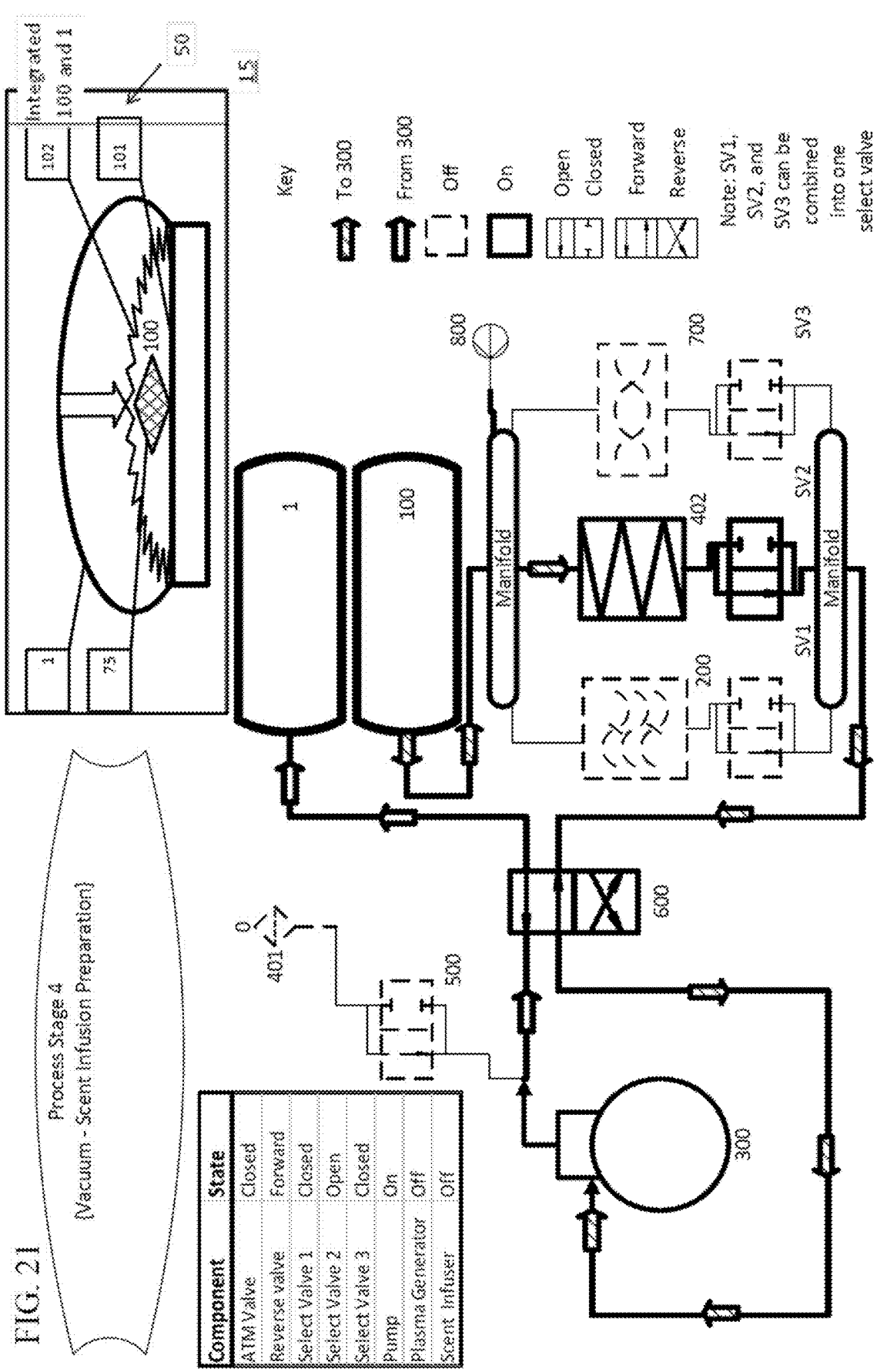

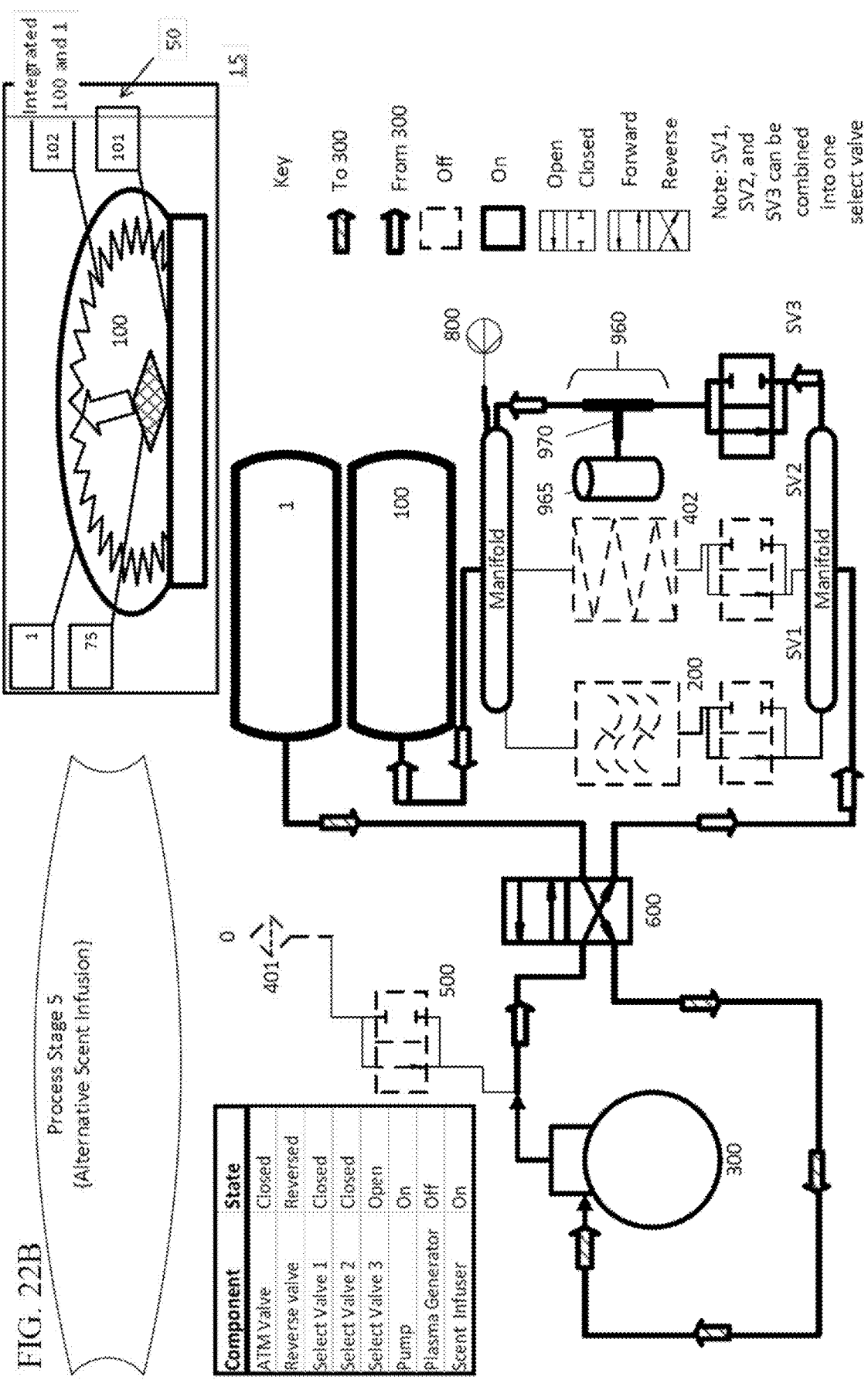

PLASMA TREATMENT DEVICE AND METHOD OF TREATING ITEMS

CROSS-REFERENCE TO RELATED APPLICATIONS

This application is a divisional of U.S. application Ser. No. 15/537,961, filed Jun. 20, 2017, now U.S. Pat. No. 10,821,199, which is the U.S. national stage application of International patent application No. PCT/US2015/067437, filed Dec. 22, 2015, which claims the benefit of U.S. Provisional Application Ser. No. 62/095,629, filed Dec. 22, 2014 and U.S. Provisional Application Ser. No. 62/129,533, filed Mar. 6, 2015, the disclosures of which are hereby incorporated by reference in their entireties, including any figures, tables, or drawings.

BACKGROUND OF INVENTION

Sterilization of surfaces and elimination of odors are common challenges in personal and professional settings. Many odors are caused by the presence of microbes and the organic substances that they produce. By eliminating microbes and their byproducts, odors can usually be controlled or eliminated. There are numerous methods, materials, and techniques utilized for this purpose. But not all items can be treated in the same way and some of the currently used techniques and substances used to control microbes or remove organic material can damage or have other undesirable effects on treated items.

Electrical generation of plasmas and reactive gases involves a process in which the potential difference between two electrode terminals exceeds the dielectric strength of the gases between the two terminals, thereby causing electrons to arc between the terminals. The interactions between the arc (coronal discharge) and dielectric gas excite the molecules comprising the dielectric gas to a higher energy state creating highly reactive products.

In addition to coronal generation, other methods of generating similarly reactive plasmas are known in the art. Highly reactive plasmas are effective for destroying organic matter through oxidation. Because of this phenomenon, reactive plasmas or gases, such as, for example, ozone, have long been used to sterilize items and eliminate odors caused by a range of sources, from smoke to microbes. Klämpfl et al. in their journal publication "Cold Atmospheric Air Plasma Sterilization against Spores and Other Microorganisms of Clinical Interest," reported that 30 seconds of physical cold atmospheric surface microdischarge (SMD) plasma operating in ambient air was very effective against different types of vegetative cells and led to a reduction of $4^{10}$ to $6^{10}$ CFU (colony-forming units).

Standard plasma sterilization devices are often ineffective and have safety issues due to the toxicity of certain plasmas. According to the EPA, breathing ozone can trigger a variety of health problems including chest pain, coughing, throat irritation, and congestion. It can also worsen bronchitis, emphysema, and asthma.

Because plasmas are generally unstable, ordinary plasma sanitization devices produce plasmas in amounts far in excess of the amount that would be required to react with the actual quantity of contaminants present on the items being sterilized. This over-production of plasma leads to inefficiencies on both the front-end plasma generation process and the back-end plasma removal process. Many devices known in the art can move or blow excessive amounts of plasma across items to be sterilized or generate an excessive amount of plasma into which items are immersed. Blowing and emersion-type sterilization devices can be inefficient and can take a long time to accomplish the sterilization task.

Still other devices utilize ozone dissolved in liquids such as water, which can flow around the items to be sterilized. Not only does this method have the same efficiency challenges, it also creates a wide range of issues with regard to dealing with the liquid itself, e.g., unnecessary weight, spills, corrosion, leaks, etc. Furthermore, many items, such as leather shoes and purses would be damaged by exposure to the liquid.

Some devices have used a vacuum to assist in the cleaning process; however, the vacuum chamber in such devices is typically rigid and not conformable or moldable to the item being cleaned. In other words, the items are not physically squeezed by a wall or walls of the chamber, making the device less efficient at removing the unwanted air residing in small openings or the pores of the items. The use of rigid walls in the vacuum chamber can also require a greater volume of plasma to refill the chamber as the negative pressure is reversed.

Other devices employ a flexible chamber to direct the flow of plasma onto articles, such as mail or parcel items in order to reduce the biological load on the articles. Typically, this method applies a continuous stream of "oxygen-containing" gas across the mail. Although such devices can limit the amount of other gases in the container, they can be inefficient and often blow ozone or other plasmas only over the surface of articles. The plasmas or other gases are not mechanically infused into the interior, the small spaces, or pores of items. Furthermore, with these devices, the gases pass through the plasma generator one time. Thus, the active "oxygen-containing" molecules entering the container must be generated on the first pass through the generator.

BRIEF SUMMARY

In accordance with the subject invention, the problem of generating a minimal amount of highly reactive plasma necessary to sterilize an object is addressed by reducing the amount of space and ambient air around and within the item. In this way, the plasma generated by the devices of the subject invention is directed at the object to be sterilized rather than non-target areas.

One embodiment of the subject invention utilizes a housing with a treatment chamber therein in which a negative pressure can be formed and maintained around an item to be sterilized. By removing the excess ambient air in the treatment chamber to create the negative pressure, the amount of plasmas required to sterilize the item is reduced. The process of removing the excess ambient air from the chamber can also facilitate the dispersion of the plasma throughout and around the item within the treatment chamber. The housing can include a top 51 and a base 52 to which the top can be attached. The base can also function as a storage area for components of the plasma treatment device. For example, a pump, valves, tubing, effluent chambers, and other components can be stored in the base. This is not a requirement of the subject invention and the components can be kept in other parts of the plasma treatment device or even apart from the plasma treatment device.

Certain embodiments employ a treatment chamber having at least one conformable wall. The conformable wall can be of a material that can be deformed, collapsed, molded, or otherwise formed around or close to the item, so as to reduce the amount of space or volume in the treatment chamber. This ability of the conformable wall to substantially conform or mold to an item to be treated and reduce the amount of non-target space around the item, can further reduce the overall amount of plasmas required. The conformable wall can also deform more pliable items, which can further facilitate the dispersion of the plasma around and throughout the spaces and pores in the item.

Other embodiments utilize a treatment chamber in the form of a pliable or flexible bag into which items can be placed and the bag sealed. With this embodiment, the entire bag can conform to the shape of the item when a negative pressure is achieved within the bag.

Yet another embodiment can have at least one effluent chamber. The removal of excess air from the treatment chamber by either pumping it to the ambient environment or sequestering it in an effluent chamber can collapse the treatment chamber, so that it substantially conforms to the shape of items in the treatment chamber. Consequently, the working volume is reduced, thereby also reducing the volume of air that has to be removed during treatment cycles. In such embodiments, during treatment cycles, the air in the working volume is passed back and forth between the treatment chamber and a secondary effluent chamber (through the plasma generator). This reduction of volume allows for less time spent pumping the air, and increased concentrations of plasma being used to treat the items.

Furthermore, in one embodiment, the present invention contemplates the use of at least one filtering mechanism to remove any excess plasma in order to protect users from potentially harmful exposure.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIGS. 3A and 3B are schematic illustrations of different configurations of a plasma treatment device according to the subject invention. These configurations include a treatment chamber, a plasma generator, an air pump and a valve to control air flow. In these configurations, air is moved to and from the ambient environment.

FIGS. 4A-4E are schematic illustrations of different configurations of a plasma treatment device according to the subject invention. The configurations shown here include a treatment chamber, a plasma generator, an air pump, a filter mechanism, and a valve to control air flow. In these configurations, air is moved to and from the ambient environment.

FIGS. 5A-5D are schematic illustrations of different configurations of a plasma treatment device according to the subject invention. The configurations shown here include a treatment chamber, a plasma generator, an air pump, a filter mechanism, and valves to control air flow. In these configurations, air is moved to and from the ambient environment.

FIGS. 6A and 6B are schematic illustrations of different configurations of a plasma treatment device according to the subject invention. The configurations shown here include a treatment chamber, a plasma generator, an air pump, a filter mechanism, and multi-directional valves to control air flow. In these configurations, air is moved to and from the ambient environment.

FIGS. 7A and 7B are schematic illustrations of different configurations of a plasma treatment device according to the subject invention. The configurations shown here include a treatment chamber, a plasma generator, an air pump, a filter mechanism, and valves to control air flow. In these configurations, air is moved to and from the ambient environment.

FIGS. 8A-8D are schematic illustrations of different configurations of a plasma treatment device according to the subject invention. The configurations shown here include a treatment chamber, a plasma generator, an air pump, a scent cartridge, and valves to control air flow. In these configurations, air is moved to and from the ambient environment.

FIGS. 9A-9H are schematic illustrations of different configurations of a plasma treatment device according to the subject invention. The configurations shown in FIGS. 9A-9D include a treatment chamber, a plasma generator, an air pump, at least one primary effluent chamber, and valves to control air flow. The configurations shown in FIGS. 9E-9H include a treatment chamber, a plasma generator, an air pump, a filter mechanism, at least one primary effluent chamber, and valves to control air flow.

FIGS. 10A-10D are schematic illustrations of different configurations of a plasma treatment device according to the subject invention. The configurations shown here include a treatment chamber, a plasma generator, an air pump, a filtering mechanism, at least one primary effluent chamber, and a valve to control air flow.

FIGS. 11A-11D are schematic illustrations of different configurations of a plasma treatment device according to the subject invention. The configurations shown here can include a treatment chamber, a plasma generator, an air pump, a scent cartridge at least one primary effluent chamber, at least one secondary effluent chamber, and one or more valves or multi-directional valves to control air flow.

FIGS. 17-23 illustrate a method by which an item can be treated using one embodiment of a plasma treatment device according to the subject invention. Included in each Figure is a schematic diagram showing the configuration of the device and/or the flow of air during the different treatment steps. Also included in each Figure is an illustration of the device showing the condition of the treatment chamber during each step. FIG. 22B illustrates an alternative scent infusion device utilizing an aerosolizing mechanism.

FIG. 25B is a cross-section of the overlay, showing how it can be placed over ports in the rigid plate.

DETAILED DISCLOSURE

Figure 1:
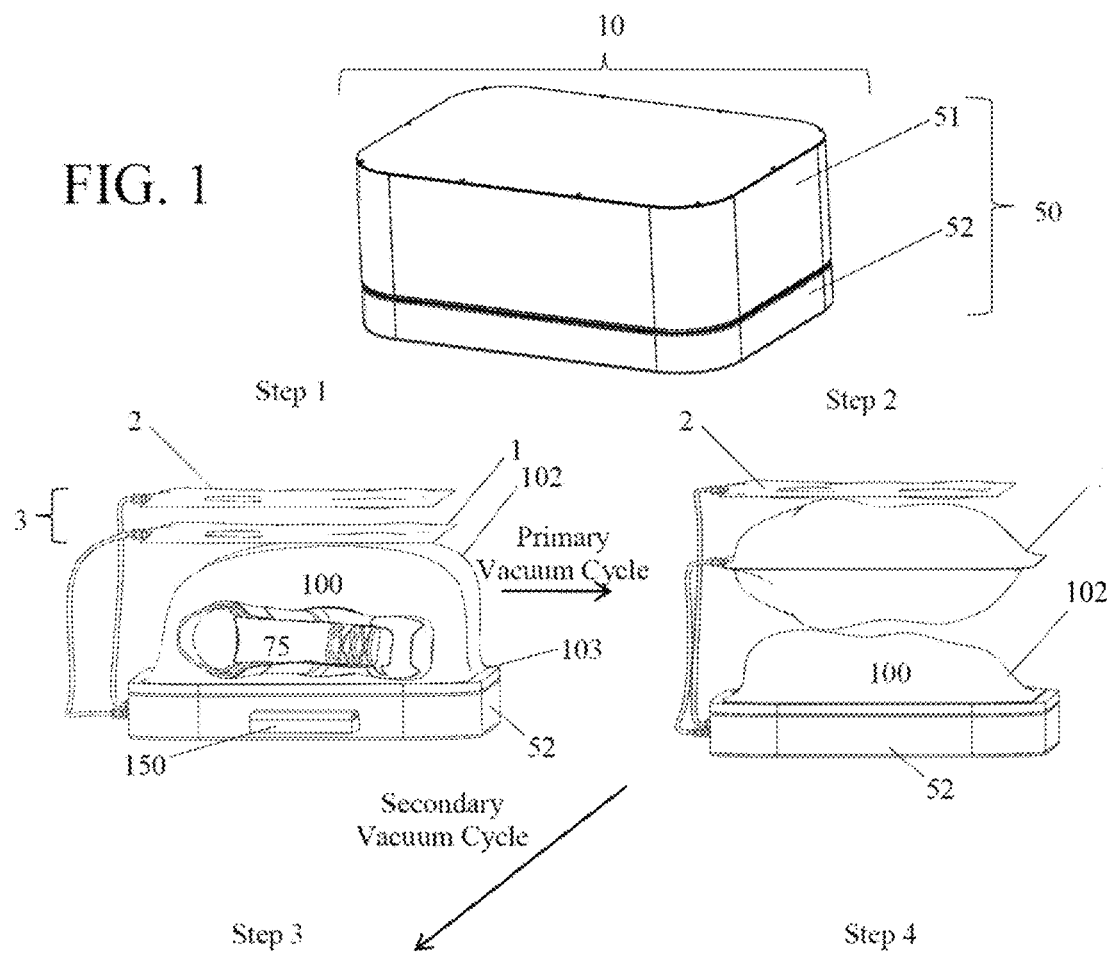
FIG. 1 shows the outside configuration of an embodiment of the housing of the subject invention. In this embodiment, the housing includes a base and a top that fits over the base.

The subject invention pertains to devices and methods for sterilization of items. More specifically, the subject invention provides embodiments of a plasma treatment chamber capable of sterilizing items placed therein. In specific embodiments, the treatment chamber is capable of being at least partially conformed to the shape of the item, so as to reduce the volume of plasma necessary to sterilize the item.

The subject invention is particularly useful for sterilizing and, in particular, controlling or eliminating odors on household or personal items, in particular, porous items or items of irregular shape, in which standard aeration or sterilization procedures may be less effective.

The terms "plasma" and "plasmas" as used with regard to the subject invention are merely for literary convenience. The terms refer to the highly reactive ions, atoms, and molecules—regardless of physical state—generated by an electric current or a coronal discharge.

The term "air" and "gas" are used interchangeably herein to describe the fluid mixtures moving throughout the device during operation.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached Figures on which the same reference numerals are used throughout to indicate the same or similar components. With reference to the attached Figures, which show certain embodiments of the subject invention, it can be seen that certain embodiments of a plasma treatment device 10 of the subject invention include a housing 50 that contains a treatment chamber 100 having the ability to be variable in size, as determined by the amount of negative pressure obtained in the treatment chamber that deforms the bag or configuration of a conformable wall 102, which can form the treatment chamber. There can further be at least one effluent chamber 3. Further, there can be at least one primary effluent chamber 1 and/or at least one secondary effluent chamber 2. Other embodiments utilize a conformable bag into which an item can be placed for treatment. A conformable bag can, but is not required to be, within a housing 50.

In one embodiment, a plasma generator 200 is employed for the purpose of forming plasma that can be pumped into the treatment chamber to sterilize and/or clean the item. Alternatively, an aerosolizing mechanism can be employed with, or in place of, the plasma generator, to effect sterilization and/or cleaning of the item. Each of these general components can have one or more sub-components, which will be discussed in detail below.

The description herein does not discuss or specifically describe the various controlling mechanisms known in the art that can be used to operate or direct the devices or components of the subject invention. Neither is the electrical wiring of the present invention discussed in detail. However, one of ordinary skill in the art would understand how the various components described herein could be attached, for example, to each other to a power supply, and the various types of controllers or operating mechanisms can be configured with the device in a manner enabling one to achieve the benefits of the subject invention. In the simplest iteration, a controller can be an actuator mechanism that moves or alters a component, such as a valve, on the plasma treatment device to effect a change in, or to advance, the treatment procedure. A controller can be operably connected to any of a variety of sensors 800 that are capable of detecting a condition and consequently the operation of the controller. Variations in types of controllers and in the attachment of the components of the subject invention that provide the same functionality, in substantially the way as described herein, with substantially the same desired results, are within the scope of this invention.

In one embodiment, the plasma treatment device 10 includes a plasma generator 200, a treatment chamber 100, and mechanism for transferring air between the plasma generator and the treatment chamber. The plasma generator can include, but is not limited to coronal, electrolytic, or ultraviolet plasma generation. Certain embodiments include flow style generators to facilitate use with air pumps 300 used with a plasma treatment device 10 of the subject invention. The various products formed by the plasma generator used in the treatment processes of the present invention may be in a gaseous or plasma state. Alternative embodiments employ aerosolized disinfectants, either in addition to, or instead of, plasma to treat items in the treatment chamber. For the purposes of this application, treatment refers to reactions with organic matter, either living or non-living, including the killing of microbes. Treatment can include the reduction or elimination of the odors associated with such organic matter.

Figure 16:
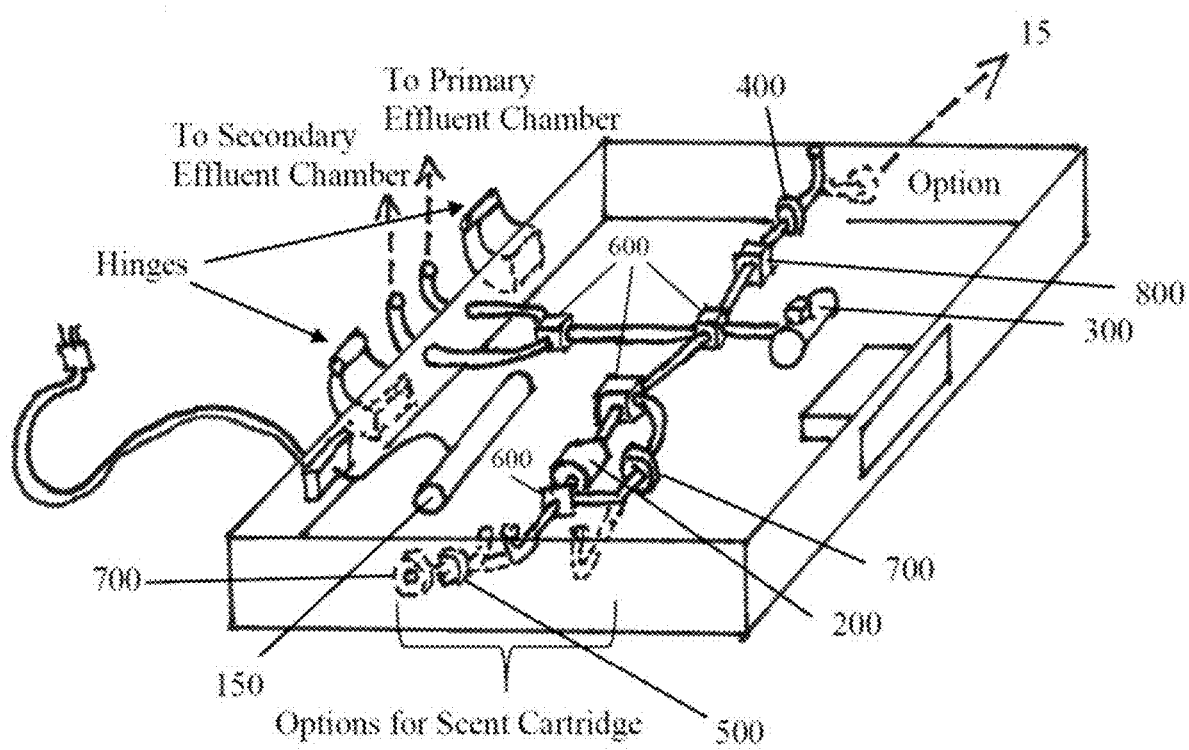
FIG. 16 is an exploded illustration of the base of the housing of one embodiment of a plasma treatment device according to the subject invention, so show how the working components can be contained entirely within the base of the device.
Figure 17:
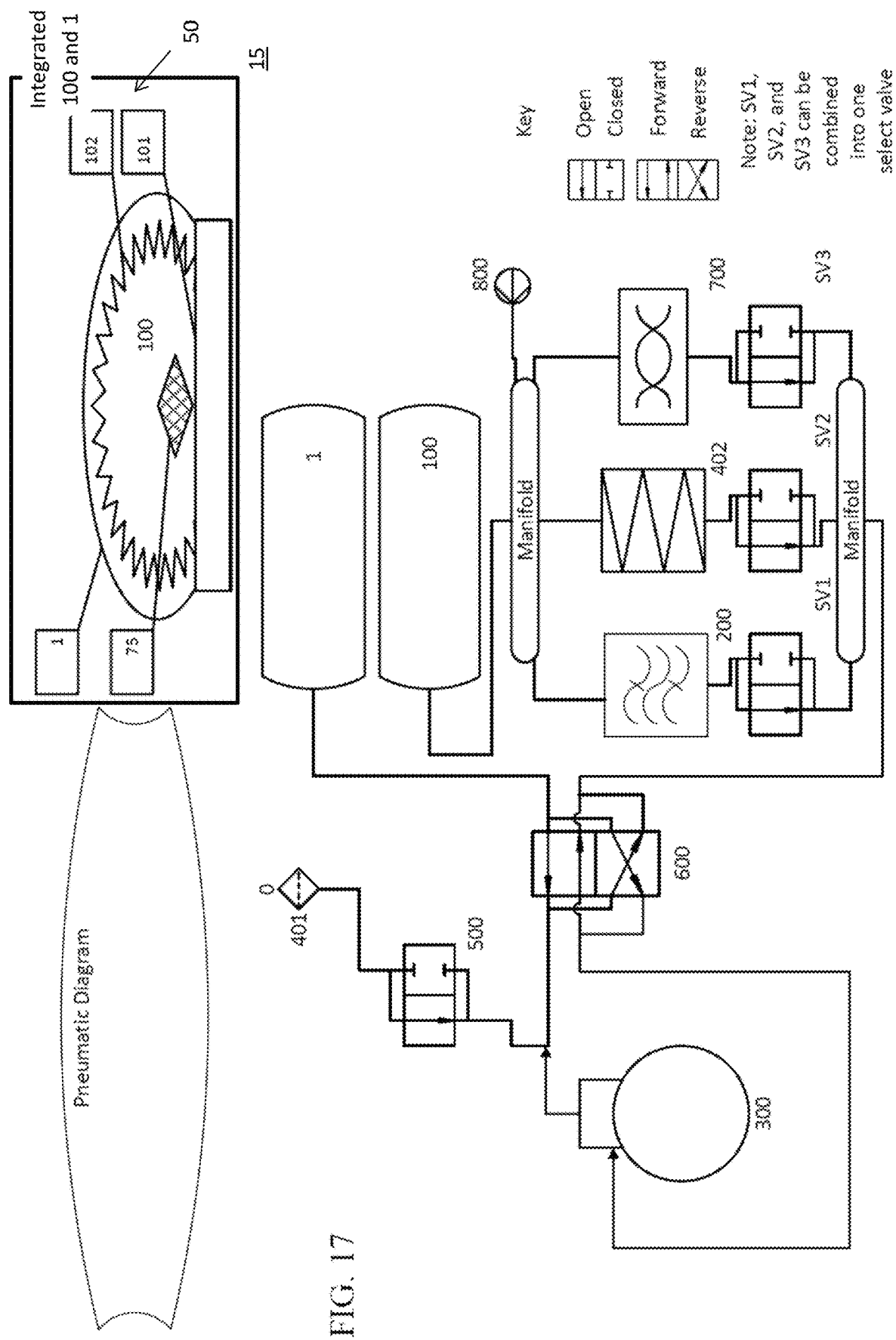
Figure 18:
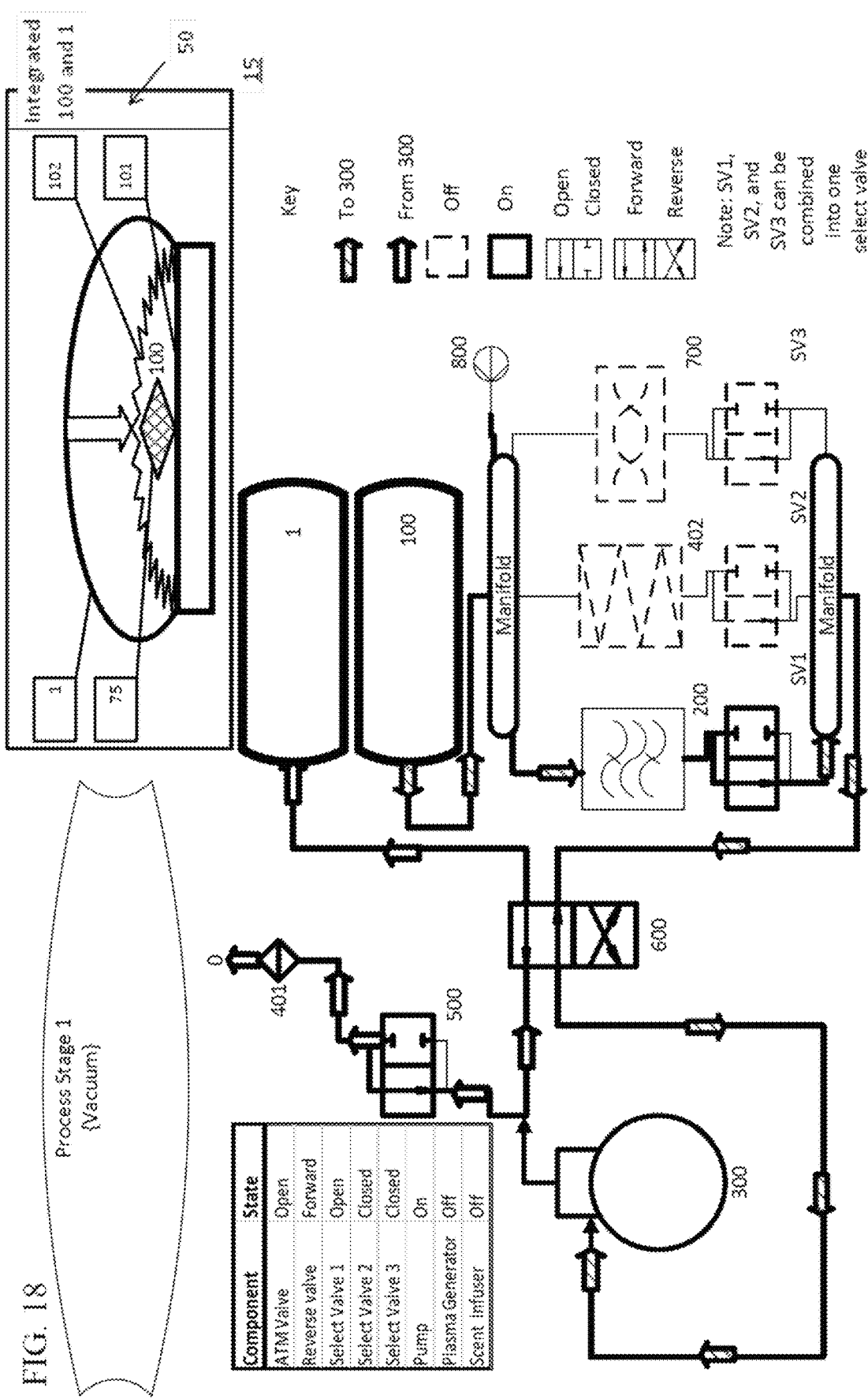
Figure 19:
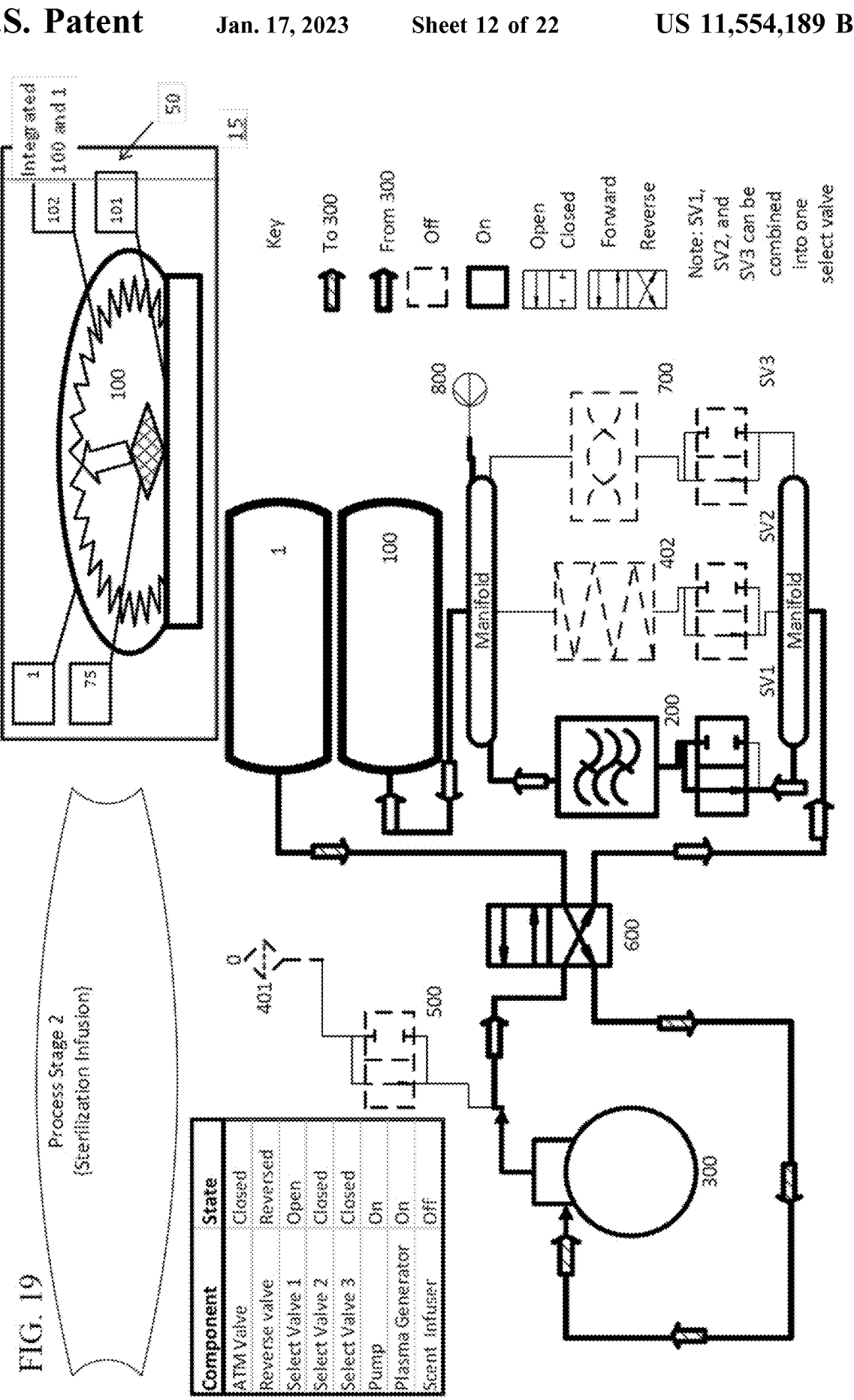
Figure 20:
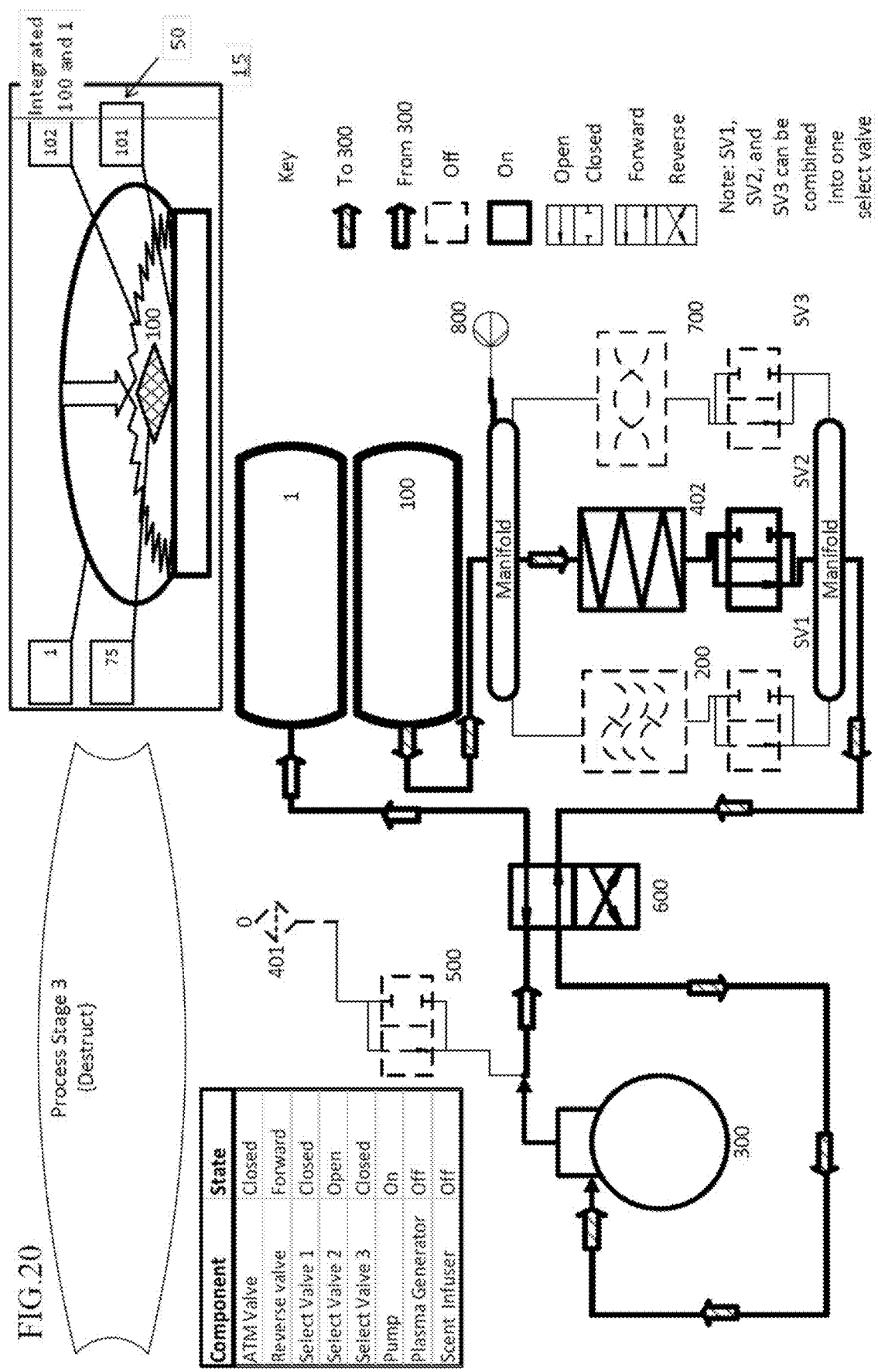

In one embodiment, the treatment chamber 100 has at least one conformable wall 102 that changes shape to at least partially surround or conform to the shape of the item(s) being treated. The conformable wall can be sealed to the rigid plate 102 using a gasket 103, an example of which is shown in FIG. 16. Materials that can be used for a conformable wall include, but are not limited to, polyethylene, polypropylene, EPDM, fluorinated hydrocarbon (such as PTFE), PEEK, or any combination thereof, or any other materials sufficiently impervious to gases, so as to retain adequate pressure differentials, and sufficiently tolerant to exposure to the various plasmas and chemical products that can be generated during the sterilization process of the subject invention.

Because the treatment chamber 100, by use of a conformable wall 102, can adjust to conform to the shape of an item being treated therein, the volume of air in the treatment chamber that must be moved during the treatment cycle(s) can also be reduced to make the device faster and more efficient. The conformability of the treatment chamber also allows the plasma treatment device 10 to squeeze or compress the items therein when sufficient negative pressure is created in the treatment chamber. This squeezing or compressing can enhance the removal of contaminants from, and the penetration of the plasma into, voids in the items. If embodiments of the subject invention utilize an aerosolized disinfectant, the negative pressure can also improve the distribution and penetration of the disinfectant into and around the material of the item. This enables the plasma generation device 10 to achieve faster, deeper treatment of porous items.

In one embodiment, the treatment chamber 100 can be formed upon closing the housing 50 of the plasma treatment device 10, such that when a top 51 of the housing is closed over and operably attached to a base 52. A rigid plate 101 can be sealed against a conformable sheet 102, with the item to be treated therebetween, such as shown, for example, in FIG. 2, in Step 1. With this embodiment, one or more of the operating mechanisms of the device 10, such as, for example, a pump, valve, tubing, wiring, and/or other components can be stored or kept within the base 52. Alternatively, the various components can be kept in other parts of the housing or even apart from the housing.

Figure 27:
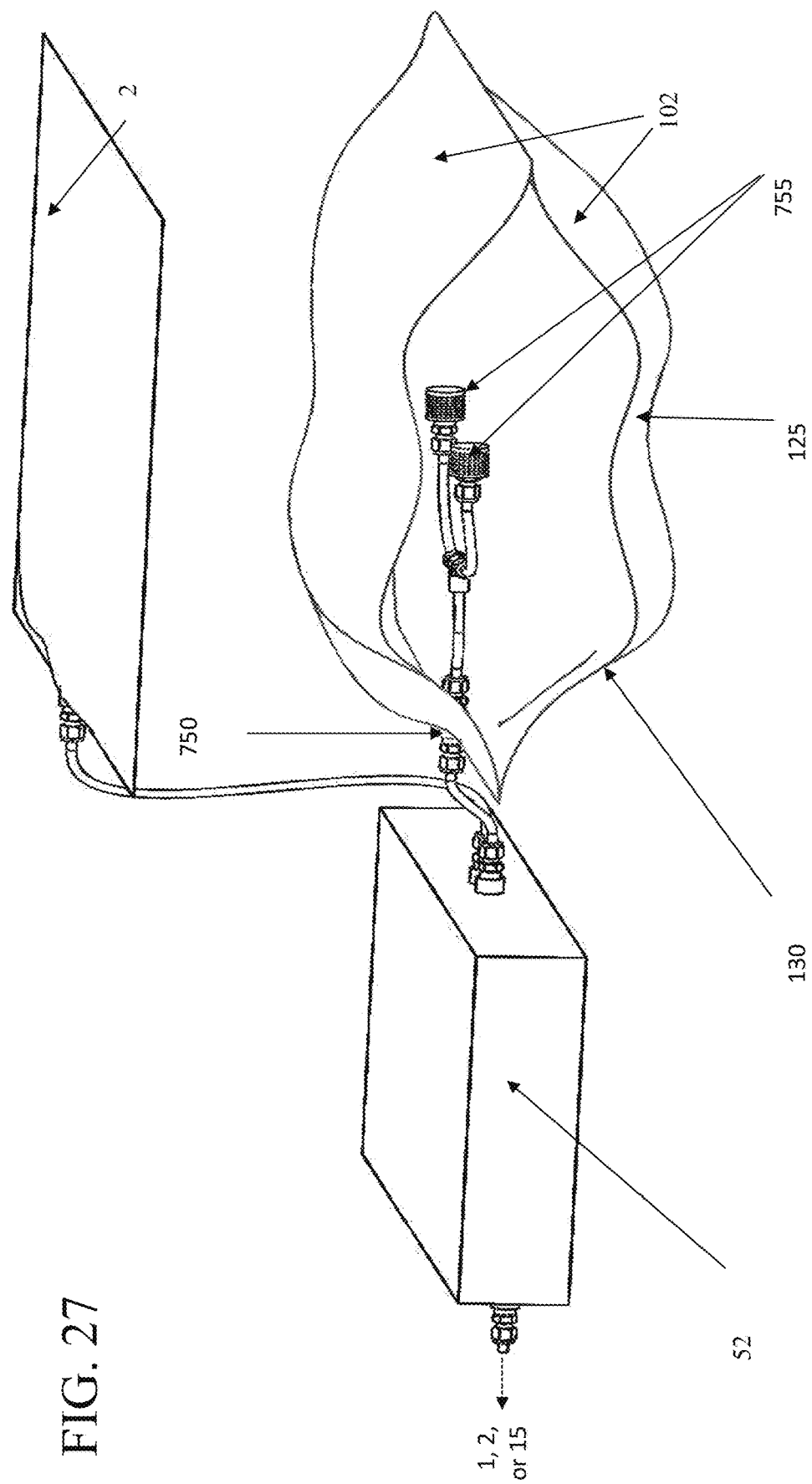
FIG. 27 illustrates an embodiment of a plasma treatment device that utilizes a conformable bag for the treatment chamber.
Figure 28:
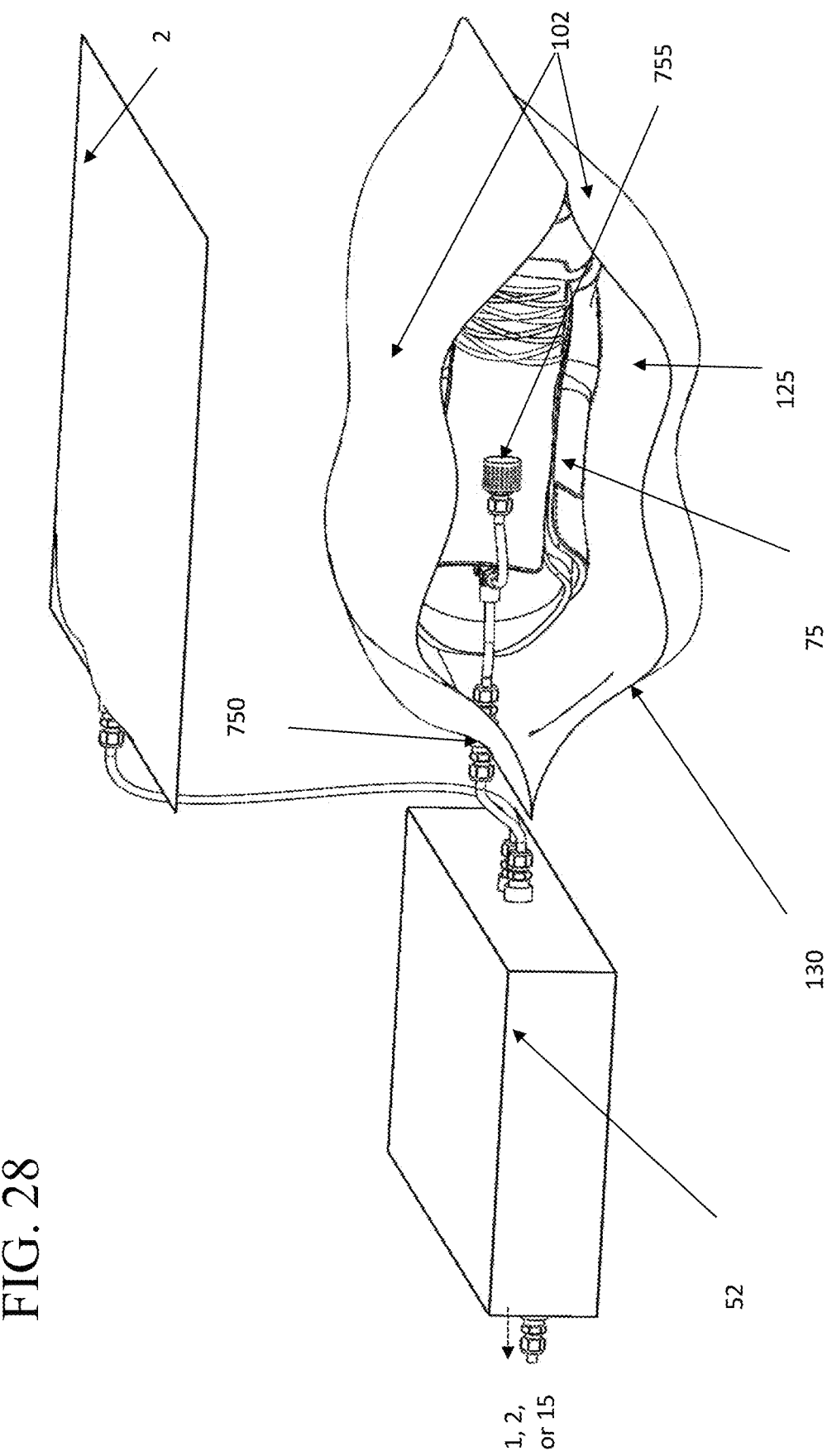
FIG. 28 illustrates the plasma treatment device in FIG. 27, with an item to be cleaned and/or sterilized placed inside the conformable bag and a gas directing component placed therein for more thorough treatment.
Figure 29:
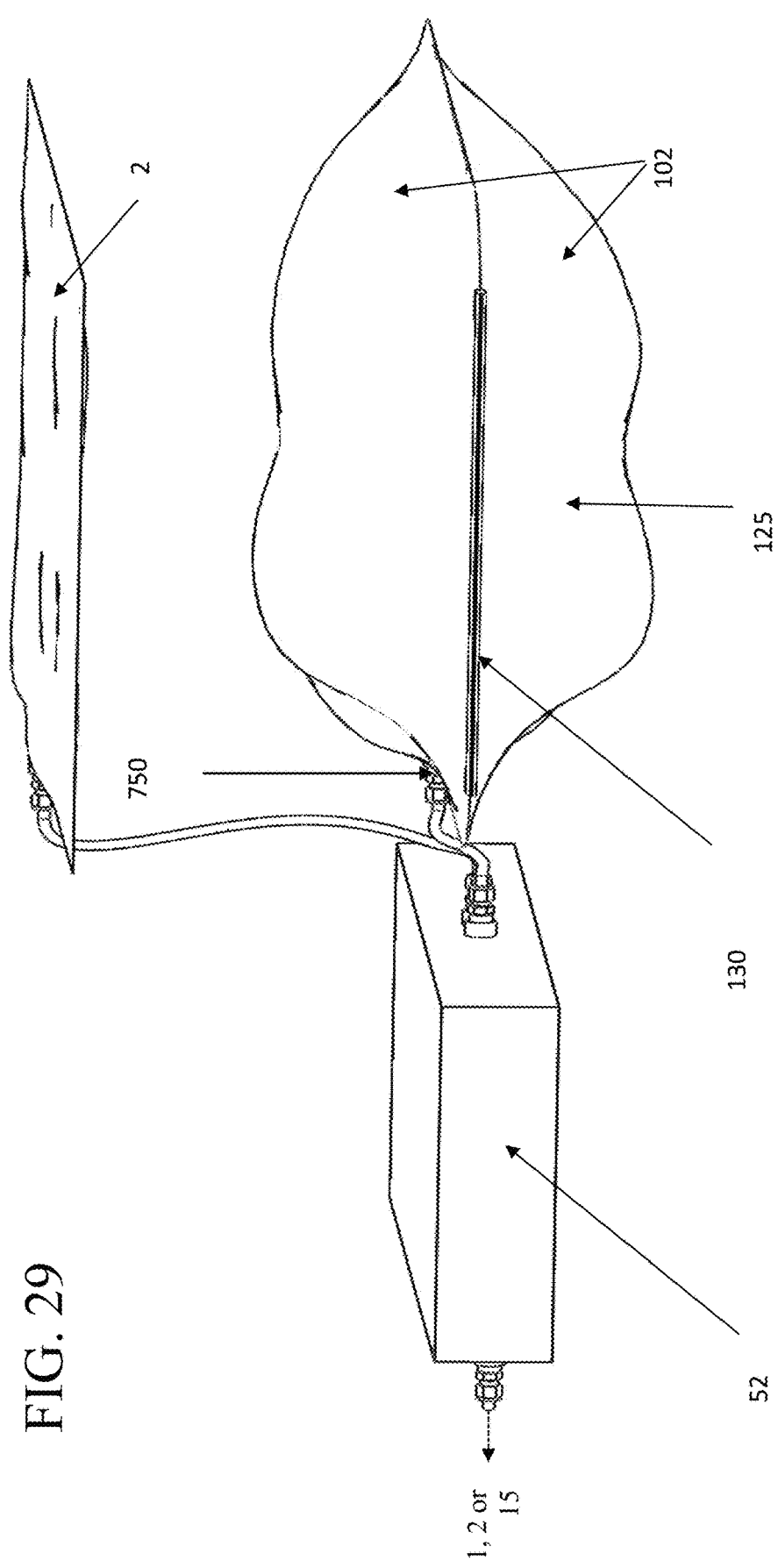
FIG. 29 illustrates the plasma treatment device in FIG. 28, after the item has been sealed therein and before the effluent chamber has been filed with the ambient air in the treatment chamber.

In other embodiments, the treatment chamber is comprised of a conformable bag 125, which has at least one conformable wall 102, such as illustrated, by way of example, in FIGS. 27, 28, and 29. A conformable bag can be operably connected to a pump 300 and any other components necessary to form a negative pressure therein and inject the desired treatment material, such as plasma or a disinfectant. In one embodiment, the conformable bag is connected to a base in which a pump and other components are stored, an example of which, is shown in FIGS. 27, 28, and 29. The formation of the negative pressure within the conformable bag can cause the at least one conformable wall to collapse towards the item, so that it conforms, at least partially, to the shape of the item.

The conformable bag can use any of a variety of sealing devices 130 and techniques known in the art. In one embodiment, the bag can utilize a reusable seal that allows the bag to be opened and closed for repeated use. For example, a slide seal or zipper seal, such as those commonly used on household storage bags, can be used, or a separate component can be attachable to the bag to affect a sufficient seal. The bag could also be sealed by folding and pinching, or any other ways that are capable of creating air-tight seals.

In one embodiment, the bag can be permanently sealed, so that an item placed therein is completely isolated from the ambient environment. With this embodiment, the conformable bag 125 can be disposable, such that after the item is cleaned and/or sterilized, the bag can be removed from the pump 300 and any other components of the plasma treatment device. A new or replacement bag can then be attached to the plasma treatment device to effect treatment of another item.

Alternatively, the bag can be reusable, having a seal 130 that allows the bag to be repeatedly opened and closed for receiving and isolating items therein. With this embodiment, the conformable bag can be permanently attached to the pump and other components. Alternatively, the bag can be removed and replaced on the plasma treatment device. To protect the conformable material of the conformable wall or the conformable bag, embodiments can include a puncture resistant lining disposed inside the treatment chamber between the conformable material and the item being treated. A person with skill in the art will be able to determine any of a variety of materials and seals that can be employed for the treatment chamber and seal embodiments of the subject invention.

The transfer of ambient air between the treatment chamber and the plasma generator may include the use of a vacuum pump 300 and air tight tubing connecting the treatment chamber 100, the plasma generator 200, and the vacuum pump. Pumps suitable for use in the present invention include, but are not limited to, oscillating piston, piston type, diaphragm, oscillating plunger, oscillating diaphragm, peristaltic, positive displacement, centrifugal, screw, blower, and rotary vane style pump.

One embodiment of a plasma treatment device has valve mechanisms 500 for directing air flow between the various components of the device. The types of valves suitable for the current invention include both flow reversing and selection valves. The flow reversing valve(s) that can be used include, but are not limited to, 4/2, 4/3, 5/2, or 5/3 valves. Multiple solenoid valves can also be arranged to allow reversing of the air flow direction in the system. The air flow reversing valve can be eliminated if a pumping mechanism is used, which allows the reversing of flow. Selection valve(s) can be any valve that allows a common inlet port to select multiple outlet ports. It should be appreciated that the air flowing between the components could travel through tubes or manifolds connected directly to one or several components.

Although pumping to and from the ambient environment 15 is possible (as shown in FIGS. 3A-8D), certain embodiments of the present invention include one or more effluent chambers 3 connected (with respect to air flow) to the treatment chamber 100. These effluent chambers can help contain the plasma and odors until such time that they can be mitigated, as well as allowing much more efficient treatment of the items. In one embodiment, the effluent chambers 3 are formed of a rigid material, such that they do not change, or can minimally change, shape as air is taken in. In an alternative embodiment, the effluent chambers are formed of a flexible or conformable material that allows for expansion and contraction as air is pumped into or out of the effluent chamber. While reference is made herein to primary and secondary effluent chambers, such references, as used herein, and unless otherwise specifically stated, are intended only to identify the presence of an effluent chamber for a particular purpose, for which there can be at least one. Thus, reference to "first" does not imply that there must be two or more. Furthermore, reference to a secondary effluent chamber does not imply that there has to be a first one. These references are not intended to confer any order in time, structural orientation, or sidedness (e.g., left or right, top or bottom) with respect to a particular feature.

One embodiment includes two effluent chambers 3, a primary effluent chamber 1 and a secondary effluent chamber 2. Each effluent chamber can be connected (with respect to airflow) to the treatment chamber 100, as shown, for example, in FIG. 2 and FIGS. 9A-11D. In this embodiment, ambient air from the treatment chamber 100 can be pumped into the primary effluent chamber 1 until certain process conditions are met. Such a process condition can be, for example, a pre-determined time limit for pumping air or when a sensor 800, such as, for example, a pressure sensor 850 indicates that a predetermined pressure has been reached in the treatment chamber 100). Air remaining in the treatment chamber after the first process condition is met can be pumped into a second effluent chamber 2.

In one embodiment, the controller can switch the device from one stage to another (for example from the primary to the secondary vacuum cycle) based upon there being achieved a specific "absolute" pressure (as measured against atmosphere) inside the treatment chamber, as measured by one or more sensors 800. In this embodiment, the pressure will be measured within the treatment chamber during the primary vacuum cycle. To determine when the treatment chamber wall has substantially conformed to the item(s), the primary vacuum cycle can continue until the pressure within the treatment chamber reaches a pre-determined pressure. This predetermined pressure level can depend, in part, on the rigidity of the conformable wall of the treatment chamber. For example, a thicker or more rigid conformable wall material can result in a lower pressure being required to conform the material to the item. One of ordinary skill in the art could determine the appropriate pressure for conforming a chamber made with a particular material by applying a vacuum to the chamber and measuring the pressure as the conformable wall collapses and conforms to an item within the chamber. For determining the end of the primary vacuum cycle (the point at which the conformable material of the treatment chamber has substantially conformed to the item within the chamber without substantially squeezing or otherwise deforming the item), the pressure sensor can determine that the pressure within the treatment chamber is slightly more negative than the pressure required to deform the conformable wall material. In one embodiment, the negative pressure level sufficient to indicate that the conformable wall 102 has substantially conformed to the item 75 could be from between approximately 0.00 PSIV to approximately −14.7 PSIV. In a more particular embodiment, the negative pressure level sufficient to indicate that the conformable wall has substantially conformed to the item can be from between approximately −0.001 PSIV to approximately −5 PSIV.

In specific embodiments, once the sensor 800 has determined, such as via pressure measurement, that the treatment chamber is substantially conformed to the item 75, a secondary vacuum cycle begins. The secondary vacuum cycle can squeeze the item by increasing the vacuum within the treatment chamber 100, thereby forcing the conformable wall to press against the items. In this embodiment, the secondary vacuum cycle will continue until at least one of three things occurs: 1) the pressure within the chamber reaches a predetermined value; 2) the pressure reaches the maximum vacuum achievable with the vacuum pump; or 3) the $\Delta P/\Delta t$ (discussed below) stabilizes or begins to stabilize.

In one embodiment, the sensor 800 operably connected to a controller will determine the end of the primary or secondary vacuum cycles based on the rate of change in pressure ($\Delta P/\Delta t$) measured in the treatment chamber. This method is less affected by changes in the conformable material in the treatment chamber, and more affected by the physical deformation characteristics of the item being treated. For instance, when treating a rigid item 75 (e.g., a lacrosse helmet) the $\Delta P/\Delta t$ at the end of the primary vacuum cycle will be much greater than when treating a softer or more pliable item of a similar size (e.g., a throw pillow). In one embodiment, the plasma treatment device 10 has different setting options based upon the type of items treated that would account for different $\Delta P/\Delta t$ value parameters being used to trigger the treatment sequences. For instance, a setting for soft items can use smaller $\Delta P/\Delta t$ values than a setting for hard items. During the primary vacuum cycle, when the excess air is being removed from the treatment chamber, the pressure inside the treatment chamber can decrease at a fairly constant rate until the chamber conforms to the item. Once the conformable wall 102 is prevented from easily collapsing (e.g., because it is contacting the item), the $\Delta P/\Delta t$ can rapidly increase. Thus, measuring the pressure, and calculating the $\Delta P/\Delta t$, allows the controller to predict when the treatment chamber wall has substantially conformed to the item, at which time the device can initiate the secondary vacuum cycle.

In a further embodiment, the $\Delta P/\Delta t$ value can be used to determine the end of the secondary vacuum cycle. Once the one or more pumps begin to reach their maximum vacuum capacity, the $\Delta P/\Delta t$ value will begin to stabilize, and the controller can then switch the device to the next stage. Again, finding the appropriate $\Delta P/\Delta t$ value for indicating the end of the primary vacuum cycle can be determined empirically by measuring the $\Delta P/\Delta t$ while observing when the conformable wall of the treatment chamber has substantially conformed to the item, but has not substantially deformed the item. The ΔP/Δt value used to indicate the end of the secondary vacuum cycle can be determined by the stabilization of ΔP/Δt value as the pumps approach their maximum vacuum or the deformation of the items stops.

Certain embodiments of the plasma treatment device 10 measure the rate of change in load (the change in current (I) over the change in time (t): ΔI/Δt) on the pump. Essentially, the same events would trigger higher ΔI/Δt values (e.g., conforming to the items and reaching maximum vacuum) as those that trigger the ΔP/Δt values, and the measurements would be used analogously.

Figure 13:
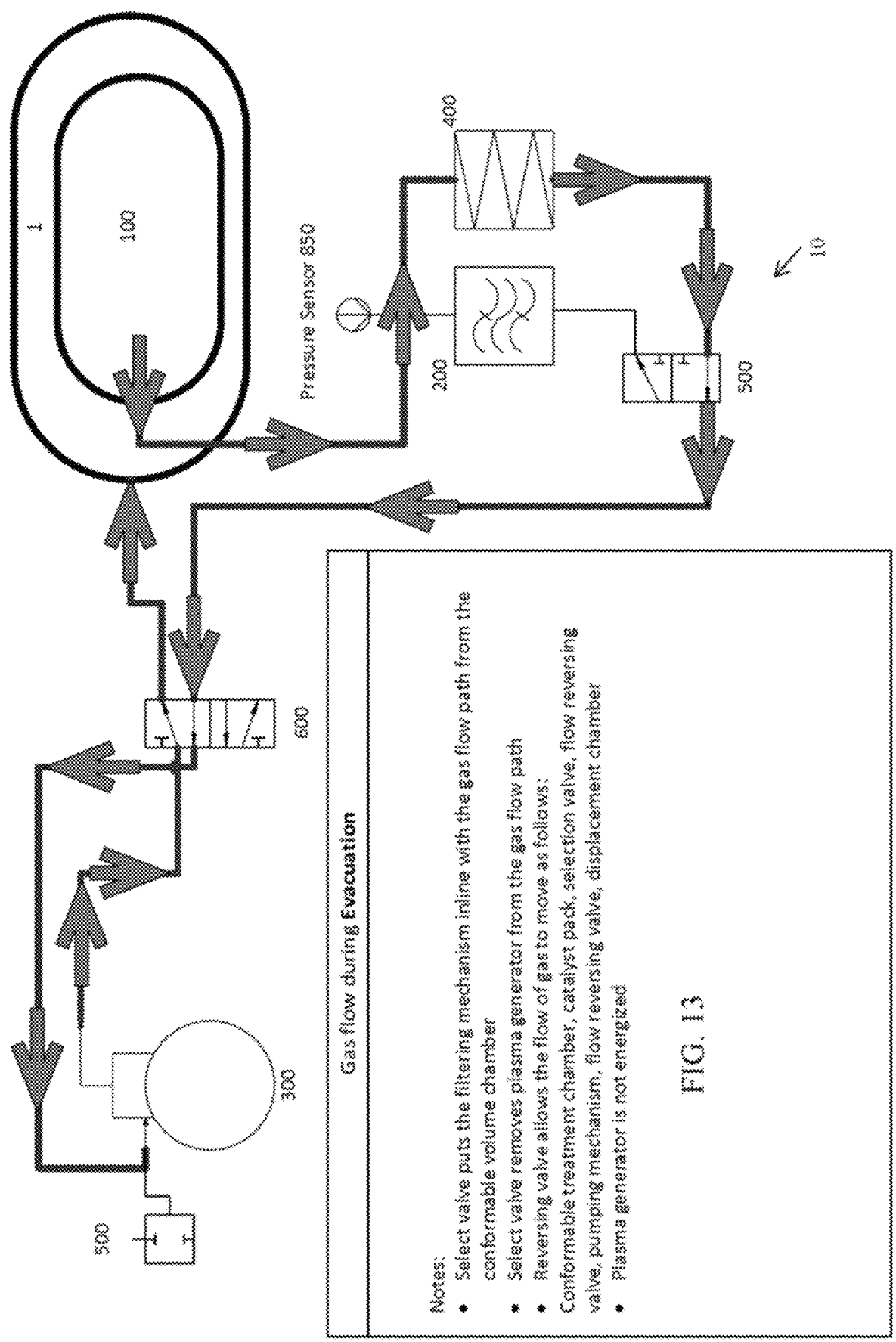
FIG. 13 is a schematic illustration of the flow of air during evacuation of the treatment chamber utilizing one embodiment of a plasma treatment device according to the subject invention.

Once a pre-determined pressure level has been reached in the treatment chamber, any of a variety of controllers can be used to operate a valve mechanism 500 that discontinues removal of ambient air from the primary effluent chamber 1 and begins to remove the remaining air from the treatment chamber so that it enters the secondary effluent chamber 2 rather than the primary effluent chamber 1, and a pump 300, operatively connected to the valve mechanism 500 would vacuum down the treatment chamber to a more negative pressure, thus, collapsing the conformable wall 102 of the treatment chamber 100 even further and squeezing or compressing the item as much as possible. FIGS. 11A-11D, FIG. 12, and FIG. 13 illustrate non-limiting examples of plasma treatment devices 10 having a primary effluent chamber 1 and a secondary effluent chamber 2. In FIG. 13, the primary effluent chamber is formed by the housing 50 and the secondary effluent chamber 2 is therewithin.

One embodiment of the device includes a vacuum reservoir system 900 to decrease treatment time. The vacuum reservoir system can include a vacuum reservoir 920 capable of withstanding a sufficient negative pressure, a high flow valve 940, capable of withstanding negative pressure and operably connected to the vacuum reservoir, and a vacuum pump that is also operably connected to the vacuum reservoir. In one embodiment, the vacuum reservoir system is operably connected to the treatment chamber, such that when the high flow valve is open, ambient air may pass from the treatment chamber into the vacuum reservoir.

In a further embodiment, when the device is powered on, and the high flow valve is closed, the vacuum pump can pull negative pressure on the vacuum reservoir to create a negative pressure chamber.

An item to be treated can initially be placed and sealed within the treatment chamber, so that the high flow valve can be opened and allow air to flow quickly from the treatment chamber to the vacuum reservoir as the pressure differential between the two chambers reaches equilibrium. Once pressure equilibrium between the treatment chamber and vacuum reservoir is reached, the high flow valve can be closed and the vacuum pump activated to again pull a negative pressure on the vacuum reservoir. If more air must be removed to reach the above-mentioned pressure parameter(s) indicating the end of the primary vacuum cycle, the primary vacuum cycle will continue until such parameter are met.

This technique of utilizing a negative pressure vacuum reservoir system allows a very rapid removal of air from a given chamber without requiring a high-flow pump. Instead, a pump can be used to slowly build up a negative vacuum "reservoir" during idle stages in the treatment process, and the high flow valve can be used to hold the negative pressure until needed.

In one embodiment, the vacuum reservoir is a rigid container disposed within the same compartment as the other components of the device. In one embodiment, the vacuum reservoir is a rigid cylindrical chamber. In another embodiment, the vacuum reservoir is a rigid container contoured to fill the voids around the other components in the storage compartment and further assist in holding them in place.

In a further embodiment, the volume of ambient air transported to and from the secondary effluent chamber 2 is passed through a plasma generator 200, as it is pumped between the secondary effluent chamber and the treatment chamber. This arrangement has several benefits including: 1) Safety—limiting volume of gas that can be converted to plasma helps prevent the device from generating potentially hazardous amounts of plasma; and 2) Efficiency—a smaller volume of air to pump between the treatment chamber and the secondary effluent chamber shortens cycle time and can result in a higher concentration of plasma being used to treat the item (especially when that small volume makes multiple passes through the generator as it moves between the chambers). This invention further contemplates using filtering mechanisms to allow the ambient environment 15 to substitute for the primary effluent chamber 1, the secondary treatment chamber 100, or both.

Figure 2:
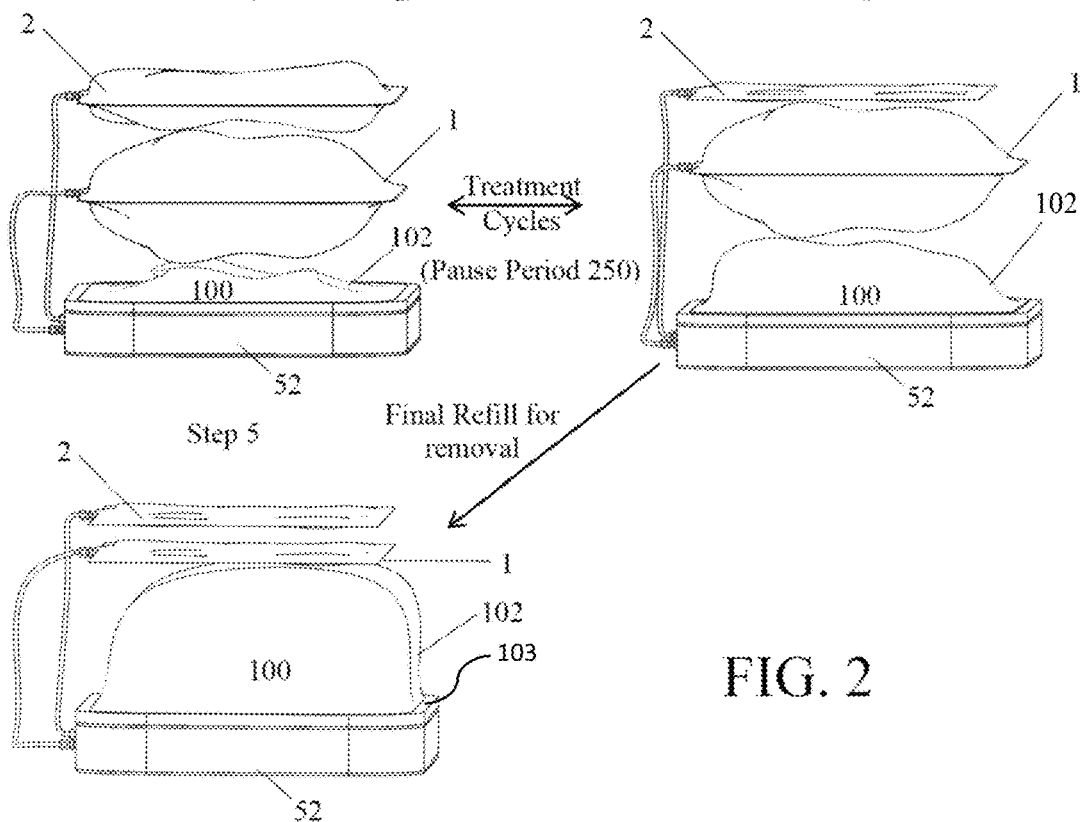
FIG. 2 shows a specific embodiment of the subject invention with the top of the housing removed to show the process of expansion and contraction of the chambers in the device during the treatment process. Step 1 shows an item placed inside the treatment chamber. For simplicity, the item is not shown in the remaining steps. In Step 2, the treatment chamber is formed when the device is closed and the edges of the conformable wall are sealed against a rigid plate. At least one hole in the rigid plate allows at least a portion of the ambient air to be pulled from the treatment chamber and sequestered in a primary effluent chamber. Step 2 shows the end of the primary vacuum cycle in which the treatment chamber conforms to the surface of the item to be treated and the primary effluent chamber, above the treatment chamber, expands as it is filled with the excess air from the treatment chamber. (Alternatively, the primary effluent chamber is not used and excess air from the treatment chamber could be emitted to the ambient environment). Once the treatment chamber has substantially conformed to the shape of the item, the secondary vacuum cycle begins. Step 3 shows the end of the secondary vacuum cycle in which the item, e.g., the boot, is further compressed and the ambient air removed during this compression is directed into the secondary effluent chamber, shown here above the first effluent chamber. Step 4 shows the partial refill of the treatment chamber as air from the secondary effluent chamber is passed through a plasma generator and into the treatment chamber. Treatment cycles occur as the ambient air is passed back and forth (through the plasma generator) between the secondary effluent chamber and the treatment chamber. Step 5 shows the final refill of the treatment chamber (with the non-plasma air in the first effluent chamber, or, alternatively, from the ambient chamber) at the end of the programmed number of treatment cycles, and the contraction of the primary effluent chamber as the air is transferred to the treatment chamber.
Figure 12:
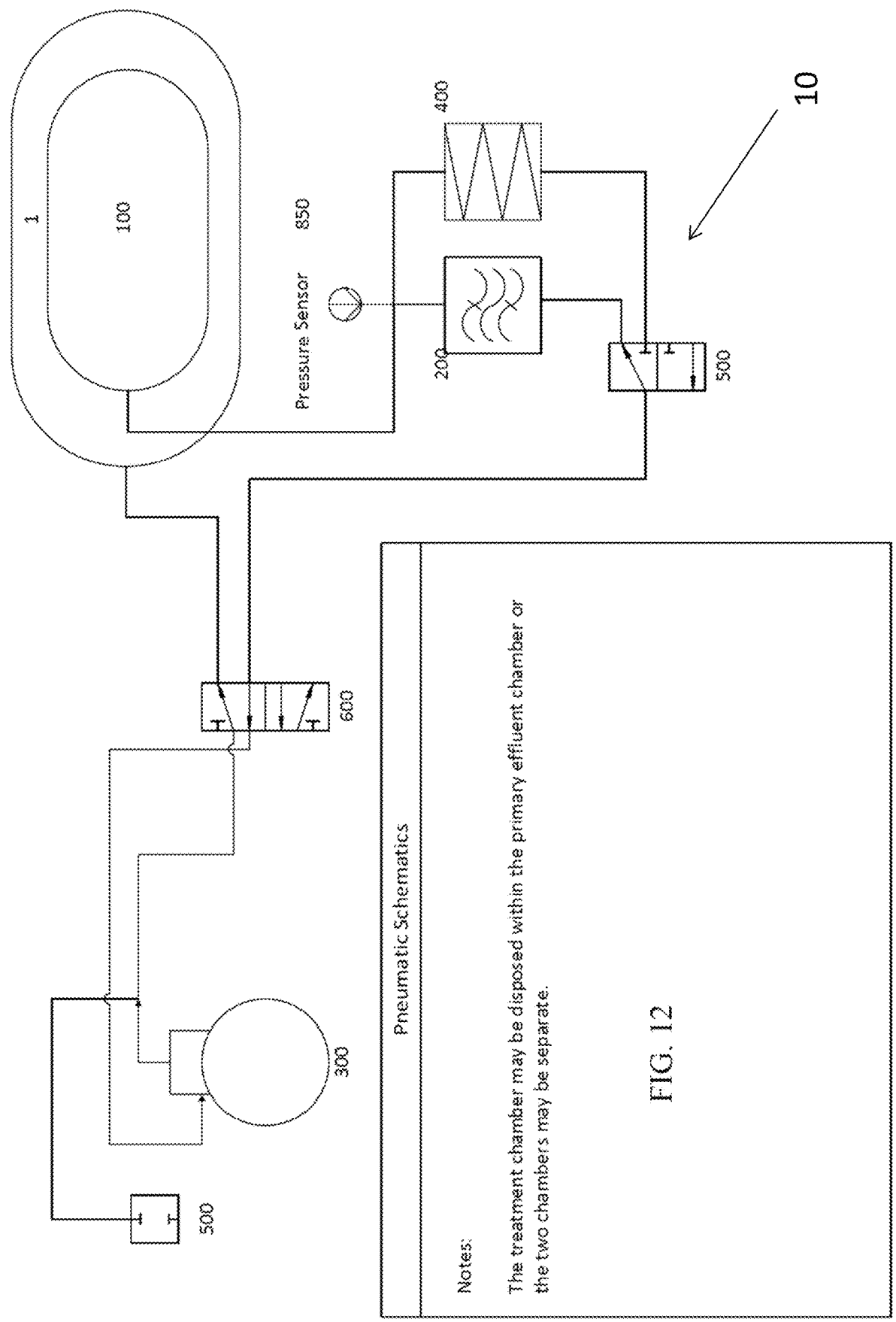
FIG. 12 is a schematic illustration showing the pneumatic configuration of one embodiment a plasma treatment device according to the subject invention.

Once the plasma has been pumped into the treatment chamber, it can surround and penetrate into the fibers, openings, pores, spaces, and contact surfaces on the item 75. The reactivity of the plasma ions can effectively and quickly begin to react with any biological or other organic material in the treatment chamber and/or on the item. To facilitate this contact, there can be a pause period 250 during the treatment cycles in which the plasma formed during that treatment cycle is allowed to remain in the treatment chamber for a pre-determined time. FIG. 2 illustrates an example of how a pause period can be incorporated into a treatment cycle. The length of a pause period can depend upon several factors that include, for example, the type of plasma being used, the size or configuration of the item, the amount of organic or biological material on the item, and other factors.

Figure 15:
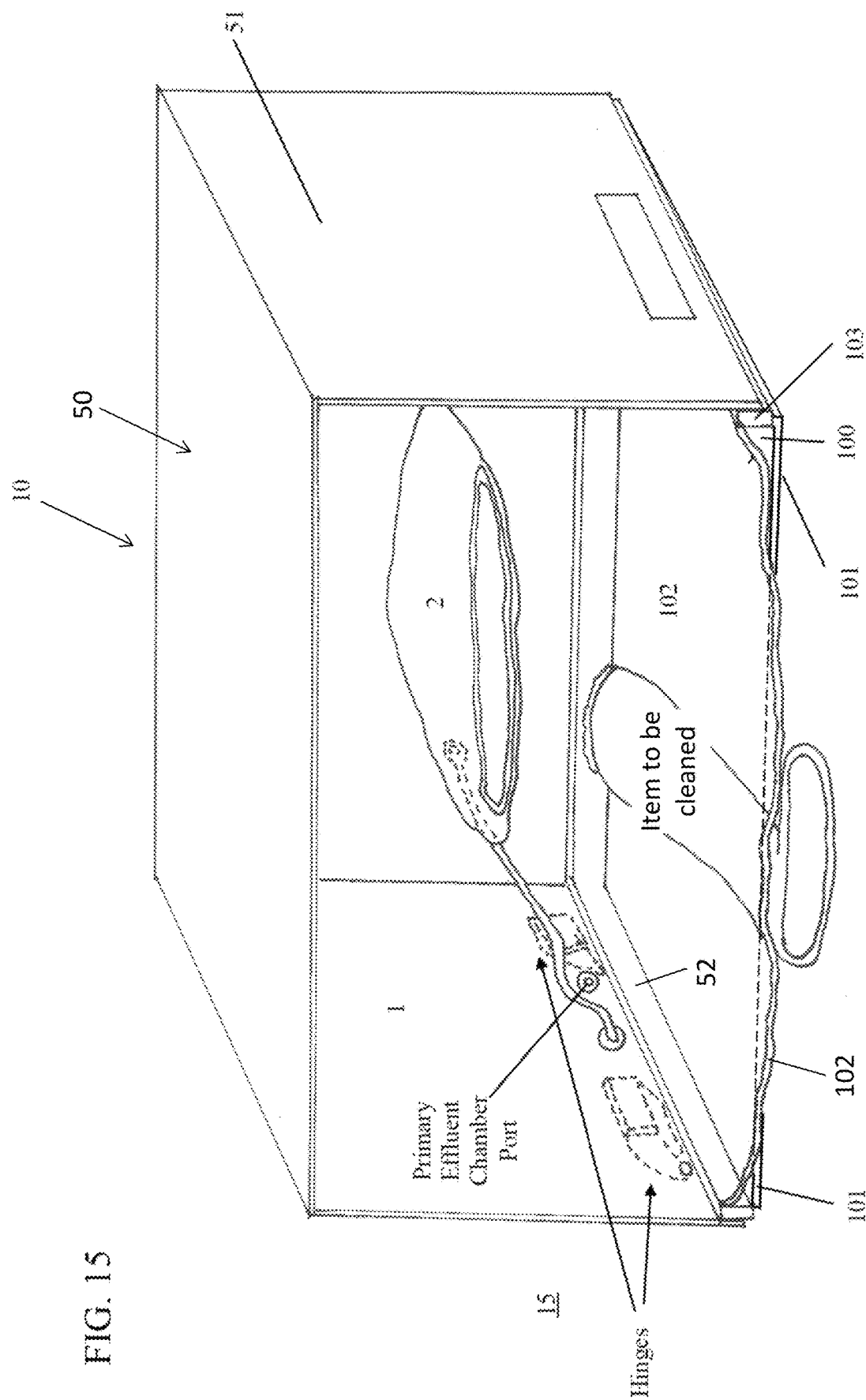
FIG. 15 is an illustration of an embodiment of a plasma treatment device according to the subject invention. In this illustration, the conformable sheet is shown collapsed around the item prior to being treated.

In one embodiment, the primary effluent chamber 1 is a rigid enclosure sealed against the outer surface of the conformable sheet 102 that forms the treatment chamber 100. With this embodiment, the primary effluent chamber can be formed by the top 51 of the housing fitting onto the base 52 and can contain both the secondary effluent chamber 2 and the treatment chamber 100 (when the device is closed), an example of which is shown in FIG. 15. In another embodiment, the primary effluent chamber 1 has at least one conformable side, or be a conformable bag. Likewise, in certain embodiments, the secondary effluent chamber may be rigid, or have at least one conformable side.

Certain embodiments of the present invention include more than one apparatus for transferring air. For example, certain embodiments can include a first pump 300 to rapidly remove the excess air from the treatment chamber into the primary effluent chamber or the ambient environment 15, and a second pump 300, with sufficient power to create or increase the negative pressure within the treatment chamber, so as to move air from the treatment chamber to the secondary effluent chamber and to squeeze the item.

It is also possible to use multiple vacuum pumps in series or parallel, including at least one embodiment in which two or more pumps can switch between parallel and series configurations. A parallel configuration allows the device to move a larger volume of air in a given amount of time, while the series configuration increases the negative pressure that can be pulled in the treatment chamber. FIGS. 4A-4E illustrate non-limiting examples of these pump configurations.

In order to monitor the pressure differentials among the various airways or chambers, which can, for example, indicate when to have the controller re-configure the valves from directing air to the primary effluent chamber 1 to directing air to the secondary effluent chamber 2, certain embodiments of the present invention also include one or more sensors 800. In one embodiment, a sensor 800 is a pressure sensors 850 capable of detecting and/or reacting to the pressure within the treatment chamber 100 and triggering any of a variety of known controlling mechanisms to initiate certain events. In another embodiment, pressure sensors 850 that respond to pressures elsewhere in the system can be used to trigger those same or other events. FIGS. 13, 14 and 17-23 illustrate embodiments that utilize pressure sensors 850. Pressure sensors and other types of sensors are known in the art for numerous purposes and device. One of ordinary skill in the art would be able to determine an appropriate sensor, either a pressure sensor, or otherwise, for use within any of the chambers described herein or one that can be connected to the gas lines that are connected to the chambers in which pressure is being measured. It is also possible, to use one more gas flow meters in certain embodiments rather than pressure sensors 850.

Figure 14:
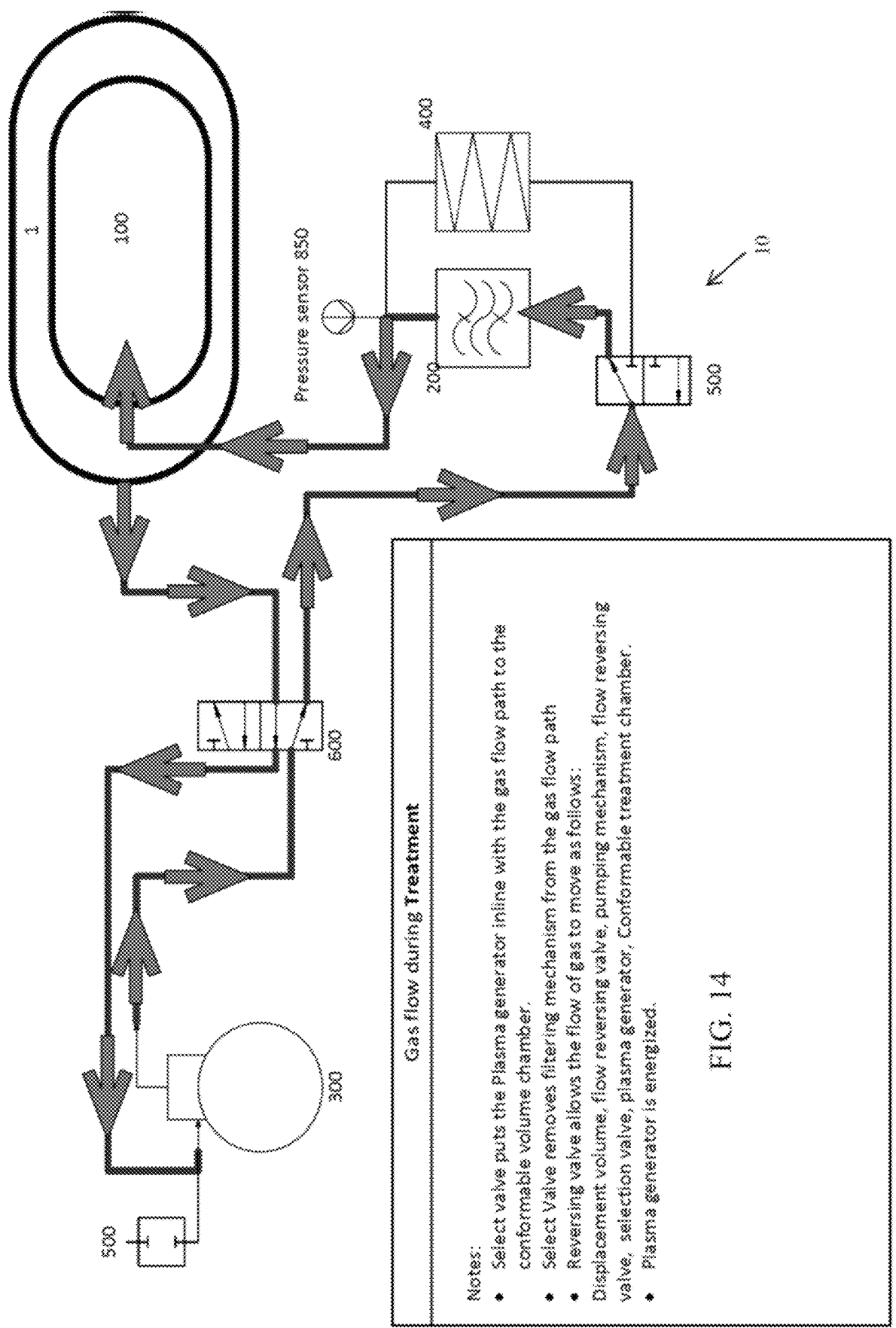
FIG. 14 is a schematic illustration of the flow of air for one embodiment of a plasma treatment device when an item is undergoing a treatment cycle according to the subject invention.

Another embodiment of the subject invention can include a filtering mechanism 400 to remove unpleasant odors emanating from the items 75 themselves, and can react with excess plasma. FIGS. 13 and 14 illustrate non-limiting embodiments that include a filter 400. In one embodiment, the filtering mechanism would be disposed (with respect to air flow) between the treatment chamber 100 and, depending upon the embodiment, either the primary effluent chamber 1, the secondary effluent chamber 2, or the ambient environment 15. Because some plasmas are considered harmful to humans, the filtering mechanism can provide another safety measure to embodiments of the subject invention. The filtering mechanism 400 can include a catalyst (such as Manganese Dioxide) that catalyzes the electrically generated plasmas to form more stable products, or the filtering mechanism 400 may be a consumable filter comprised of a reactant material (such as carbon or oxidizable metals, such as, for example, iron) which will react with the electrically generated plasmas to form more stable products. A filtering mechanism 400 can also have a combination of catalyst and consumable filter. An embodiment of the filtering mechanism 400 using a consumable filter can be a replaceable cartridge.

One embodiment, shown by way of example in FIGS. 17-23 utilizes at least one odor filtering mechanism 401 to remove odors from the air exiting the treatment chamber 100 during the primary vacuum cycle and at least one other plasma filtering mechanism 402 to remove excess plasmas from the ambient air after the treatment cycles are completed. For additional safety, certain embodiments include a detection mechanism to determine the level of plasma removal from the treatment chamber prior to unlocking the treatment chamber after a treatment cycle.

A further embodiment includes a scent cartridge 700 operably connected (with respect to air flow) to the treatment chamber, one example of which is shown in FIG. 16 and in FIGS. 17-23. In this embodiment, after the programmed number of treatment cycles is completed, air can be passed actively (such as, for example, pumped or forcibly passed) or passively (such as, for example, by releasing a valve holding negative pressure in the treatment chamber, allowing intake of ambient environment air) through the scent cartridge 700 into the treatment chamber 100 to impart an odor to the items being treated. In such embodiments, the scent cartridge 700 may be disposed (with reference to the air pathways) either in series or in parallel with the plasma generator. In another embodiment, a scent cartridge 700 may be disposed (with respect to the air pathways) either in series or parallel with an air pump 300. A scent cartridge 700 may also be disposed in series with a valve and operably attached to the treatment chamber 100. In such embodiments, the valve may be disposed on the treatment chamber 100 side of the scent cartridge 700 or on the side of the scent cartridge 700 that is opposite the treatment chamber 100. In certain embodiments, the present invention further utilizes the scent cartridge with the filtering mechanism. In a specific embodiment, the scent cartridge is combined with the filtering mechanism.

Other devices and techniques can be combined with the embodiments of the subject invention to increase the effective reduction in living microbes on an item. One embodiment, includes a UV light source 150 positioned to emit UV light onto the items in the treatment chamber. UV light devices have been used to kill microbes in hospital rooms and other settings. The embodiments of the current invention utilizing a UV light source can have an increased antimicrobial effect. FIGS. 2 and 16 illustrate non-limiting examples of how a UV light source can be incorporated with embodiments of the subject invention.

Figure 24:
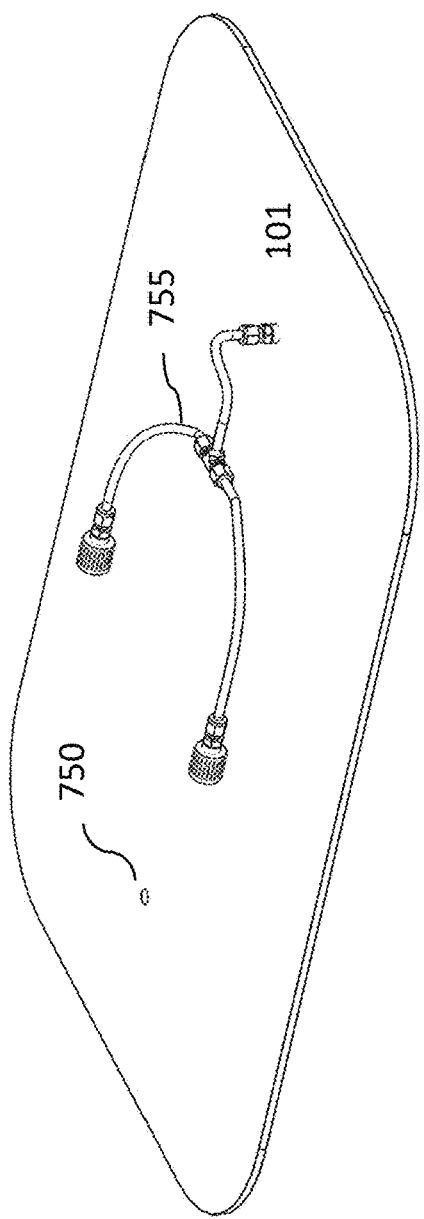
FIG. 24 is an illustration of one embodiment of a gas directing component. In this embodiment, a port within the rigid plate has attached a hose or tube that can be directed at specific areas of an item for more direct or intense sterilization.
Figure 25A:
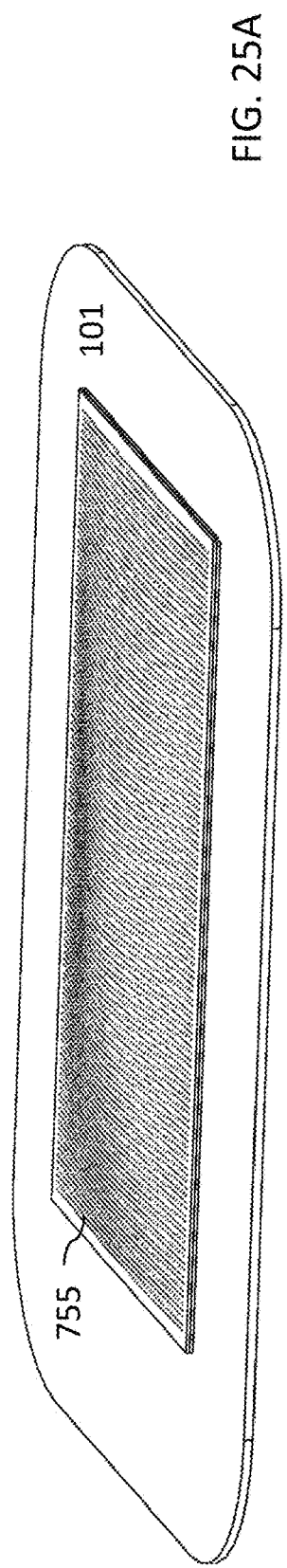
FIGS. 25A and 25B illustrate an alternative embodiment of a gas directing component. This embodiment utilizes an overlay having a plurality of smaller openings that can overlay one or more ports within the rigid plate, such that gas is diffused through the overlay upwards towards the item.
Figure 25B:
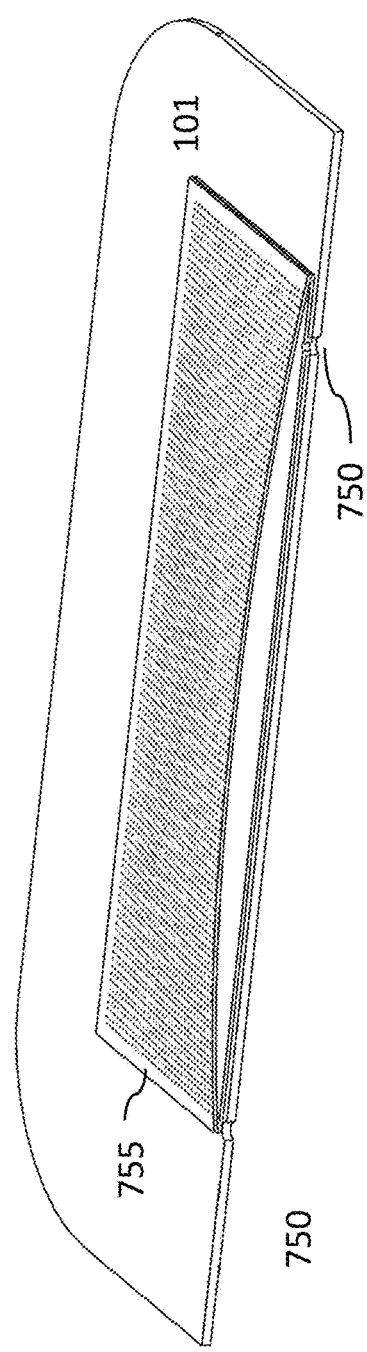
Figure 26:
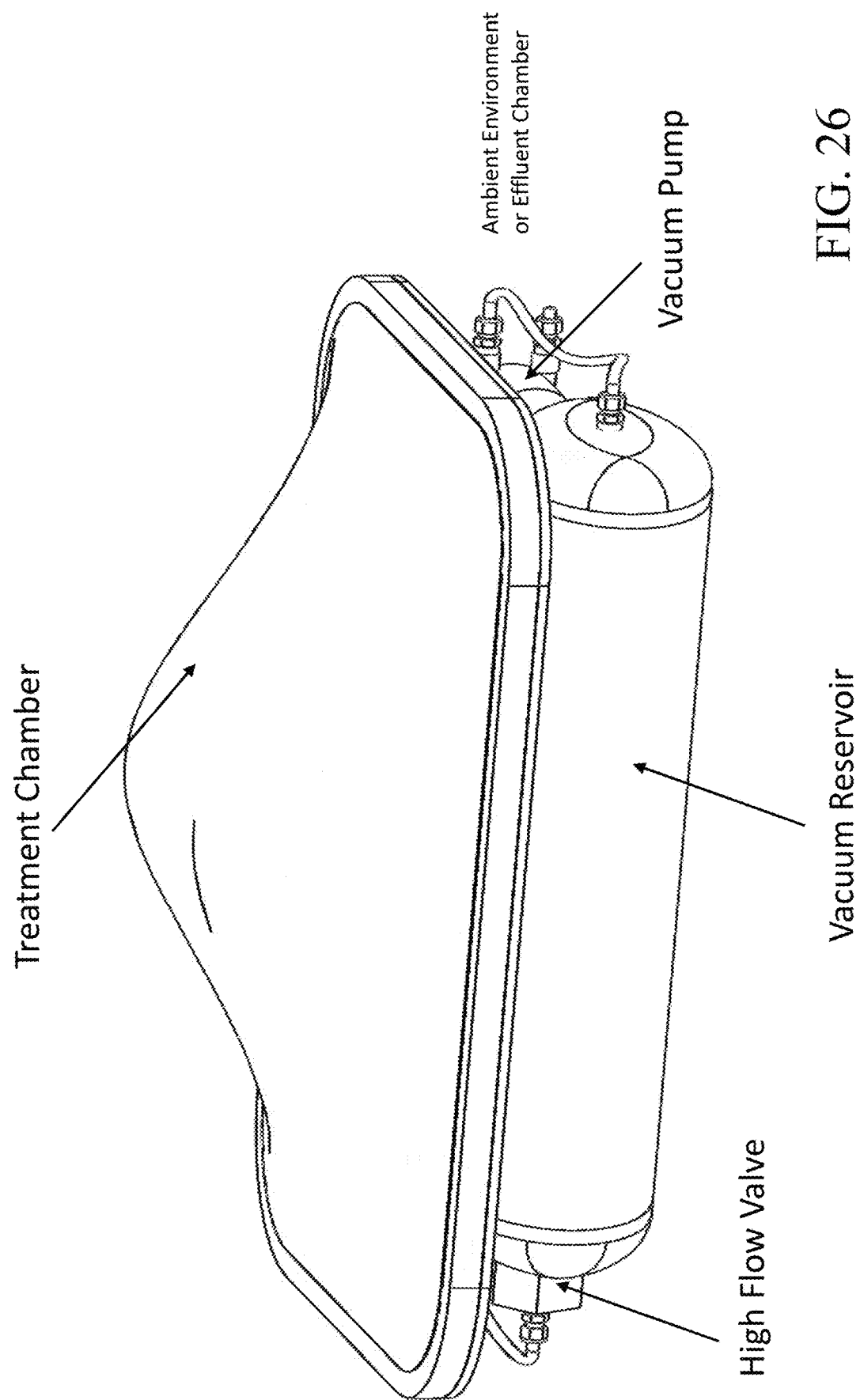
FIG. 26 illustrates one embodiment of a vacuum reservoir system that can be utilized with embodiments of the subject invention.

Certain items can have areas, spaces, or structures thereon that may require additional or more direct application of the air containing the treatment material, such as the plasma or disinfectant, to achieve the desired effect of killing microbes and removing odors. An additional feature of the embodiments of the subject invention can be the ability to direct the treatment air in a way that maximizes the treatment of certain items. One embodiment of the subject invention has a plurality of ports 750 leading into the treatment chamber, one example of which is shown in FIGS. 24 and 25B. FIGS. 27, 28, and 29 illustrate a conformable bag. Not only can these ports be disposed in particular patterns to adjust flow of treatment air into and out of the treatment chamber, but they also allow for particular arrangements of gas directing components 755, such as hoses, funnels, or diffuser to be attached to the ports to enhance treatment of certain articles. For example, to treat the interior of boxing gloves, it may be desirable to have the treatment gases passed directly into, and out of, the interior of the gloves.

One embodiment includes a gas directing component in the form of a flexible tube attached to at least one of the ports, an example of which is shown in FIG. 24 the end of the tube being insertable into the interior of the item, such as a glove, to direct gasses into and out of the interior of the item during treatment cycles. Alternatively, it may be desirable to have a more general diffusion of the gasses into and out of the treatment chamber—for example, when treating a towel. In another embodiment a plurality of ports 75 in the walls of the treatment chamber, such as, for example, in the rigid plate 101 can be used. In still another embodiment, a diffusion attachment can be attached over one or more of the ports, such as shown, for example in FIGS. 25A and 25B.

A plasma treatment device 10 of the subject invention is not limited to treating a specific size item 75. The size of any item that can be treated is limited only by the dimensions and/or volume of the treatment chamber 100. In one embodiment, a plasma treatment device can be hand-portable and suitable for household use. For example, a plasma treatment device of the subject invention that can useful for treating a household item or clothing can have a treatment chamber sized to fit into a portable housing 50. In another embodiment, a portable treatment device can be permanently located, or is at least not hand-portable, and have a treatment chamber sized to contain larger items or have industrial or commercial use. In one embodiment, a treatment chamber has a volume between approximately 50 ml and approximately 500 liters. In a more specific embodiment, a treatment chamber has a volume between approximately 200 ml and 50 liters.

The devices of the subject invention can be used to treat items by employing a repeatable process that includes a vacuum stage and a refill stage. One embodiment of the process is shown in FIGS. 17-23. During the vacuum stage of the process, shown for example in FIG. 18, negative pressure is pulled on a treatment chamber 100 having a conformable wall 102, such that the conformable wall collapses onto the item and can further squeeze or compress the item being treated, for the purpose of removing as much ambient air as possible from the treatment chamber. During the refill stage of the process, seen in FIG. 19, the negative pressure is reversed or released within the treatment chamber until a point of neutral or positive pressure is obtained. One vacuum stage followed by one refill stage constitutes one treatment cycle. In a particular embodiment, the vacuum stage and the refill stage are repeated multiple times to perform multiple treatment cycles.

Figure 22A:
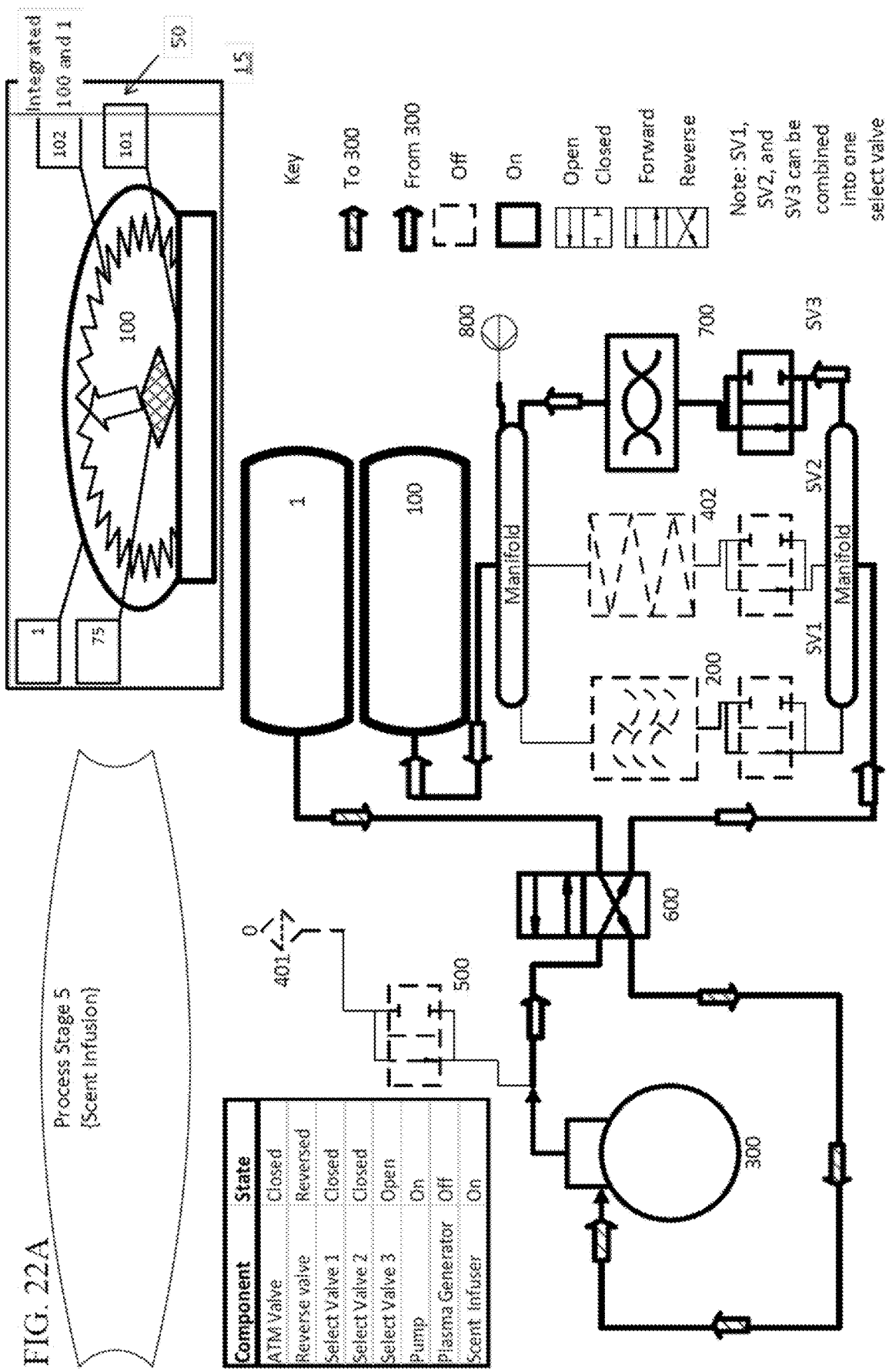
Figure 23:
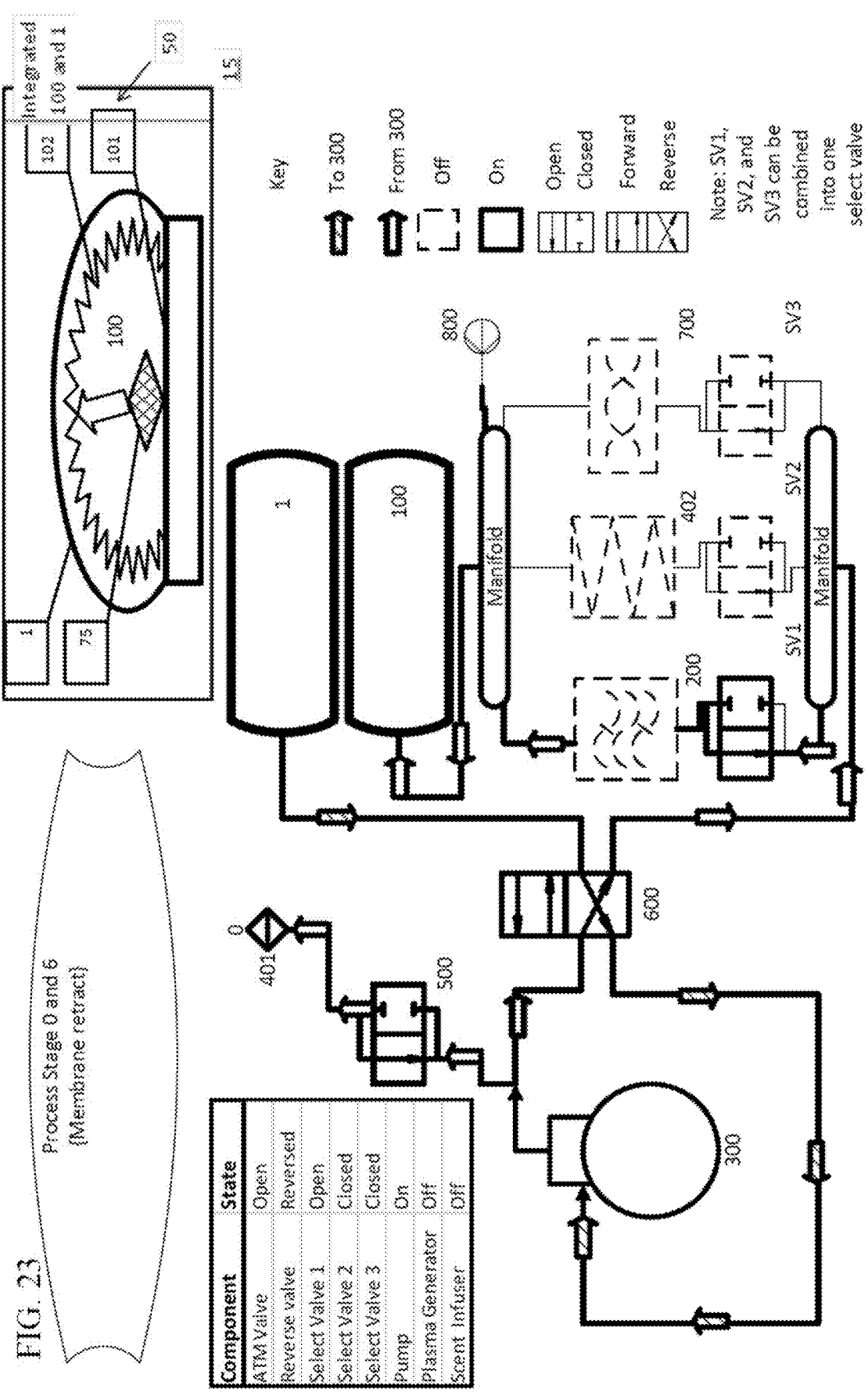

In a further embodiment, there is a final cycle that occurs after the multiple treatment cycles. In the final cycle, air is passed into the treatment chamber until the pressure within the treatment chamber returns to at, or approximately, neutral pressure, at which time the item can be removed from the treatment chamber, which is shown in FIG. 23. In a particular embodiment, during a final cycle, air is passed through a scent cartridge prior to entering the treatment chamber, as shown in FIGS. 22 and 23, thus imparting a scent to the item being treated.

Specific embodiments of the method utilize plasma to treat items within the treatment chamber. In such embodiments, the air entering the treatment chamber during the refill stage passes through a plasma generator 200 prior to entering the treatment chamber 100. Because the plasma is highly reactive, it can attack organic matter in the items. Destruction or inactivation of organic matter on the items can have an odor neutralizing, a deodorizing, or antimicrobial effect.

In an alternative embodiment, aerosolized disinfectants in addition to, or instead of, plasma can be used to treat the items. Examples of such aerosolized disinfectants include, but are not limited to, hydrogen peroxide and alcohols. One embodiment of the device incorporates an aerosolizing mechanism 960 to apply aerosolized disinfectants to the items 75 when ambient air is moved back into the treatment chamber 100. FIG. 22B illustrates a non-limiting example of this embodiment. In this embodiment, the disinfectant can be utilized during each treatment cycle or during the last refill cycle. In certain embodiments, the aerosolizing mechanism includes a fluid reservoir 965 to hold the disinfectant and a nozzle 970 for aerosolizing the fluid disinfectant so that it passes into the ambient air pathway. Examples of an aerosolizing nozzle that can be used with the embodiments of the subject invention include, but are not limited to, Venturi style or jet orifice nozzles or any other nozzle known in the art that can create sufficiently small droplets of liquid from a reservoir so that they can be carried to the treatment chamber by the ambient air flow. In a further embodiment, the aerosolizing mechanism would preferably be connected to the ambient air pathway leading into the treatment chamber, and the aerosolizing mechanism can be activated while ambient air is being passed into the treatment chamber, such that the aerosolized disinfectant is infused into the treatment chamber as it refills. In an alternative embodiment, the aerosolizing mechanism is used to disperse a scented fluid instead of or in addition to the disinfectant fluid.

The vacuum stage of the process can include a primary and a secondary vacuum cycle. In embodiments including a secondary vacuum cycle, the primary vacuum cycle first removes the ambient air from the treatment chamber 100, causing the conformable wall 102 of the treatment chamber to begin conforming to the item and creating a reduced working volume of air within the treatment chamber. The removal of ambient air during a primary vacuum cycle does not have to, but can, create a negative pressure within the treatment chamber. This step in the process can be followed by the secondary vacuum cycle that can pull at least a minimal negative pressure on the treatment chamber and moves all or most of the remaining, reduced working volume of ambient air. The secondary vacuum cycle can remove the remaining ambient air, either directly or through a plasma generator, into an effluent chamber. Then, during the refill stage, the air from that effluent chamber is passed back through the plasma generator and into the treatment chamber. Subsequent treatment cycles move the reduced volume of air back and forth (through the plasma generator) between the effluent chamber and the treatment chamber. Reducing the working volume reduces the amount of time required to pump the air back and forth, and increases the efficiency of the treatment (as explained above).

As discussed above, certain embodiments of the plasma treatment device utilize a sealable 130 conformable bag 125, having at least one conformable wall 102, as the treatment chamber 100. A conformable bag can utilize any of the methods and components described herein for the embodiments using a conformable wall 102 sealed against a rigid plate 101. In embodiments using the conformable bag as a treatment chamber, sealed inlet and outlet ports can be created to allow air to flow in and out during the cycling. The ports may also include attachments for gas directing components. In such embodiments the treatment chamber may be either enclosed in a housing 50 or, in alternative embodiments, the treatment chamber is not enclosed within a housing. An example of when it would be beneficial not to have the treatment chamber enclosed would be when using the device to treat very large items (e.g., a mattress). In such embodiments, the item to be treated would be placed into the conformable bag, and the opening of the bag would be sealed closed.

The methods of treating an item using a plasma treatment device 10 of the subject invention can be initiated when the item is placed into the treatment chamber 100 and the treatment chamber 100 is closed. A primary vacuum cycle can then begin. In one embodiment, during the primary vacuum cycle, air is removed from the treatment chamber 100 and passed either directly or through a filtering mechanism 400 into the ambient environment 15. The primary vacuum cycle can continue until the controller is activated, when one or more process conditions are met (for examples, when a time limit is reached or when a pressure sensor 850 indicates that a predetermined pressure has been reached in the treatment chamber 100). Then, the controller can activate the plasma generator 200 and a refill cycle can be initiated, wherein air is transferred (either actively—using the air pump 300 to drive the air, or passively—merely opening a valve to allow the relative pressures to equilibrate) from the ambient environment 15 through the activated plasma generating electrode 200, which generates plasmas.

The active or passive transfer of the air that passes the plasmas into the treatment chamber 100 can continue until the sensor 850 determines that one or more process conditions are met, as described above, and activates a controller 850. In one embodiment, the controller initiates a treatment pause for a predetermined amount of time while the plasmas are in the treatment chamber for sterilizing the items. After the treatment pause, the controller can be activated to begin the primary vacuum cycle again and the air is once more pumped from the treatment chamber 100, through a filtration mechanism, and into the ambient environment 15 until the sensor determines that one or more process conditions are met.

In a further embodiment, the controller can initiate additional treatment cycles (depending on the programmed regime) in which the controller activates the plasma generator 200 and switches the flow of air so that it flows from the ambient environment 15 through the plasma generator 200 and the plasmas pass into the treatment chamber 100. After the last treatment cycle, the controller can initiate a final vacuum cycle in which the air from the treatment chamber 100 is pumped back, either directly or through a filtering mechanism 400, into the ambient environment 15. After completing the programmed number of treatment cycles and the final vacuum cycle, the controller can initiate a final flow cycle in which air from the ambient environment 15 is passed (actively or passively) into the treatment chamber 100 until a sensor determines that certain process conditions are met (for example, a time limit, or when a pressure sensor 850 indicates that a predetermined pressure has been reached in the treatment chamber 100). In certain embodiments, the final flow cycle passes air from the ambient environment 15 directly into the treatment chamber 100 or, in other embodiments, through a scent cartridge 700 to make the items fragrant. Once the sensor determines that the entire treatment regime has completed, the items may be removed from the treatment chamber 100.

In one embodiment, during the primary vacuum cycle, air is removed from the treatment chamber 100 and passed directly, through a filtering mechanism 400, or through an activated plasma generator 200, into a primary effluent chamber 1. In such embodiments, the primary vacuum cycle continues until a sensor 800 operably connected to the controller determines that certain process conditions are met (for example, a time limit, or when a pressure sensor 850 indicates that a predetermined pressure has been reached in the treatment chamber 100) indicating the end of the primary vacuum cycle.

In embodiments in which the plasma generator has not been activated at the outset of the primary vacuum cycle, once the primary vacuum cycle ends, the controller can activate the plasma generator 200 and air can then be passed (either actively or passively) from the primary effluent chamber 1 through the activated plasma generating electrode which generates plasmas that are then passed into the treatment chamber 100 until the sensor determines and activates the controller when certain process conditions are met (for example, a time limit, or when a pressure sensor 850 indicates that a predetermined pressure has been reached in the treatment chamber 100).

If the plasma generator 200 is activated at the outset of the primary vacuum cycle, the generator 200 can remain activated after the primary vacuum cycle ends and the air is passed from the primary effluent chamber 1 through the generator 200 and then into the treatment chamber 100. The controller can then initiate a treatment pause for a predetermined amount of time allowing time while the plasmas are sterilizing the items. After the treatment pause, the controller begins the primary vacuum cycle again and the air is once more pumped from the treatment chamber 100 through a filtration mechanism and into the primary effluent chamber 1.

In an alternative embodiment, the air is pumped directly from the treatment chamber 100 to the primary effluent chamber 1 without passing through a filtration mechanism, until the sensor 800 determines that certain process conditions are met (for example, a time limit, or when a pressure sensor 850 indicates that a predetermined pressure has been reached in the treatment chamber 100) and activates the controller.

In one embodiment, the controller initiates additional treatment cycles (the number depending on the programmed regime) in which the controller activates the plasma generator 200 and switches the flow of air so that it flows from the primary effluent chamber 1 through the plasma generator 200 and the plasmas pass into the treatment chamber 100. After the last treatment cycle, the controller initiates a final vacuum cycle in which the air from the treatment chamber 100 is pumped back into the primary effluent chamber 1. After completing the programmed number of these treatment cycles and the final vacuum cycle, the controller initiates a final flow cycle in which air from the primary effluent chamber 1 is passed (actively or passively) into the treatment chamber 100 until the controller is activated by a sensor that determines that the desired process conditions are met. In one embodiment, the final flow cycle passes air from the primary effluent chamber 1 directly into the treatment chamber 100 or, in another embodiment, through a scent cartridge 700 to impart a scent to the item 75. Once the entire treatment regime has completed, the items may be removed from the treatment chamber 100.

In one embodiment, when the controller initiates the primary vacuum cycle, air is removed from the treatment chamber 100 and passed either directly or through a filtering mechanism 400 into a primary effluent chamber 1. In at least one embodiment, the primary vacuum cycle continues until the controller is activated by a sensor that determines that process conditions are met, such as described above. The controller can initiate a secondary vacuum cycle in which the air from the treatment chamber 100 is pumped into a secondary effluent chamber 2—the secondary effluent chamber 2 may also be conformable to allow it to expand or contract. When the process conditions are met, such as, when the pressure sensor 850 indicates that a predetermined pressure has been reached in the treatment chamber 100, for example, there is, a lower pressure than the pressure inside the treatment chamber 100 that triggered the termination of the primary vacuum cycle, the controller can activate the plasma generator 200 and switch the flow of air so that it flows from the secondary effluent chamber 2 through the plasma generator 200 and the plasmas pass into the treatment chamber 100. One example of this method is shown in FIG. 2.

In a further embodiment, the controller can initiate a treatment pause for a predetermined amount of time while the plasmas are sterilizing the items. The controller begins the secondary vacuum cycle again and the air is once more pumped from the treatment chamber 100, either through a filtration mechanism, through the plasma generator, or directly, into the secondary effluent chamber 2 until it has been determined that certain process conditions are met. Next, the controller may initiate additional treatment cycles (the number depending on the programmed regime) in which the controller activates the plasma generator 200 and switches the flow of air so that it flows from the secondary effluent chamber 2 through the plasma generator 200 and the plasmas pass into the treatment chamber 100. Among the several benefits achieved by this method is the smaller volume of air that has to be passed back and forth between secondary effluent chamber and the treatment chamber, which enables the device to treat the items more efficiently. This method can also require less time to complete each treatment cycle. Also, in embodiments in which the air is passed through the plasma generator on its way back and forth from the treatment chamber and the secondary effluent chamber, the amount of air that is converted to plasma will increase, thus increasing the concentration of plasma used to treat the items.

In at least one embodiment, when the controller initiates the primary vacuum cycle, the air from the treatment chamber 100 is pumped to the ambient environment 15 (either directly or through a filtering mechanism 400). In at least one embodiment, the primary vacuum cycle continues until the controller determines that certain process conditions are met. Next, the controller initiates a secondary vacuum cycle in which the valves are switched to allow air to be pumped from the treatment chamber 100 into a secondary effluent chamber 2. In one embodiment, the secondary effluent chamber 2 is conformable to allow it to expand or contract. When the sensor determines that certain process conditions are met, the controller can activates the plasma generator 200 and switches the flow of air so that it flows from the secondary effluent chamber 2 through the plasma generator 200 and the plasmas pass into the treatment chamber 100. The controller then initiates a treatment pause for a predetermined amount of time while the plasmas are sterilizing the items. After the treatment pause, the controller begins the secondary vacuum cycle again and air is once more pumped from the treatment chamber 100, either through a filtration mechanism or directly into, the secondary effluent chamber 2, again, until the sensor determines that certain process conditions are met. The controller can initiate additional treatment cycles (depending on the programmed regime) in which the controller activates the plasma generator 200 and switches the flow of air so that it flows from the secondary effluent chamber 2 through the plasma generator 200 and the plasmas pass into the treatment chamber 100.

After the last treatment pause, the controller may initiate a final flow cycle in which the air from the treatment chamber 100 is pumped through a filter mechanism into the ambient environment 15 until the controller determines that certain process conditions are met. The valves are switched to pump air from the ambient environment 15, directly or through a scent cartridge 700, into the treatment chamber 100 until the controller determines that certain process conditions are met. Once the controller determines that the entire treatment regime has completed, the items may be removed from the treatment chamber 100.

The examples and embodiments described herein are for illustrative purposes only and various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of treating a surface to kill microbes and/or reduce odor, wherein said method comprises exposing the surface to a treatment chamber of a device, wherein said device comprises:
    a treatment chamber comprising at least one conformable wall for forming a volume adjacent to the surface to be treated;
    at least one pump operably connected to the treatment chamber, such that at least a portion of ambient air in the treatment chamber is removable by the at least one pump, thereby creating a negative pressure that causes the conformable wall to collapse, so as to reduce the volume of the treatment chamber leaving a working volume of air in the treatment chamber;
    an effluent chamber that receives, from the at least one pump, and sequesters at least a portion of the working volume from the treatment chamber and from which the at least one pump returns the working volume to the treatment chamber; and
    a plasma generator positioned such that the working volume in the at least one effluent chamber passes through the plasma generator as it is removed from the at least one effluent chamber and into the treatment chamber, whereby at least a portion of the working volume returned into the treatment chamber is converted to plasma;
    wherein the method comprises,
    placing the surface into the treatment chamber,
    performing a primary vacuum cycle comprising,
    a first stage comprising activating the at least one pump operably connected to the treatment chamber, such that, a portion of ambient air in the treatment chamber is removed by the at least one pump, thereby creating a negative pressure that reduces the volume of the treatment chamber by causing the conformable wall to collapse and at least partially conform to the surface, while retaining a working volume of air in the treatment chamber;
    performing a secondary vacuum cycle comprising,
    removing the working volume, with the at least one pump, to the effluent chamber;
    returning the working volume, with the at least one pump, to the treatment chamber;
    passing the working volume through a plasma generator as the pump returns the working volume to the treatment chamber, thereby converting at least a portion of the working volume to plasma;
    performing a final cycle comprising,
    removing the working volume from the treatment chamber, with the at least one pump; and
    moving air from outside the treatment chamber into the treatment chamber, thereby restoring volume to the treatment chamber.
2. The method according to claim 1, wherein the secondary vacuum cycle is repeated at least once, thereby increasing the concentration of plasma in the working volume returned to the treatment chamber.

3. The method according to claim 1, further comprising removing at least a portion of the ambient air from the treatment chamber, during the primary vacuum cycle, to another effluent chamber.

4. The method according to claim 1, wherein the device further comprises at least one filter, and the method further comprises at least one of moving the at least a portion of the ambient air in the treatment chamber through the filter during the primary vacuum cycle and moving the working volume in the treatment chamber through the filter during the final cycle.

5. The method according to claim 4, wherein the at least one filter deactivates or removes the plasma from the working volume.

6. The method according to claim 1, wherein the treatment device further comprises a scent cartridge and the final cycle further comprises passing the air from outside the treatment chamber into the treatment chamber through the scent cartridge.

7. The method according to claim 1, further comprising the at least one pump moving the working volume into the at least one effluent chamber until the negative pressure in the treatment chamber reaches a predetermined $\Delta P/\Delta t$ value.

8. The method according to claim 7, wherein the $\Delta P/\Delta t$ value is between approximately −0.001 PSIV and approximately −5 PSIV.

9. The method according to claim 1, further comprising the at least one pump moving the working volume into the at least one effluent chamber until at least one of a) the pressure within the treatment chamber reaches a predetermined value; b) the pressure reaches the maximum vacuum achievable with the at least one pump; or c) the $\Delta P/\Delta t$ stabilizes.

10. The method according to claim 1, further comprising moving air outside the treatment chamber into the treatment chamber, subsequent to creating the negative pressure during the primary vacuum cycle, thereby increasing the working volume in the treatment chamber.

11. The method according to claim 1, wherein the treatment chamber further comprises one or more ports and the method further comprises the at least one pump removing the working volume through the one or more ports.

12. The method according to claim 11, wherein the treatment chamber further comprises a gas directing component that leads into the treatment chamber from at least one of the one or more ports and the method further comprises moving all or a portion of the working volume through the gas directing component during the secondary vacuum cycle.

13. The method according to claim 1, wherein the device further comprises a vacuum reservoir system operably connected to the treatment chamber and the method further comprises:
  a) activating the at least one pump to remove air in a vacuum reservoir of the vacuum reservoir system to create a negative pressure therein;
  b) opening a valve between the vacuum reservoir and the treatment chamber, during the primary vacuum cycle, causing at least some of the ambient air in the treatment chamber to be pulled into the vacuum reservoir until the ambient air equilibrates between the vacuum reservoir and the treatment chamber; and
  c) closing the valve to retain the ambient air pulled into the vacuum reservoir.

14. The method according to claim 13, further comprising:
  repeating, at least once, steps a), b), and c) until the negative pressure in the treatment chamber reaches a predetermined $\Delta P/\Delta t$ value.

15. The method according to claim 1, wherein the treatment chamber comprises a volume of between approximately 50 ml and approximately 500 liters.

16. The method according to claim 1, wherein the treatment chamber comprises a volume of between approximately 200 ml and approximately 50 liters.

17. The method according to claim 1, wherein the device further comprises an aerosolizing mechanism between the at least one pump and the treatment chamber, the aerosolizing mechanism comprising:
  a reservoir for containing a material;
  a nozzle between the reservoir and the treatment chamber that aerosolizes the material;
  wherein the method further comprises at least one of moving the aerosolized material into the treatment chamber with the working volume during the secondary vacuum cycle and moving the aerosolized material into the treatment chamber with the air from outside the treatment chamber during the final cycle.

18. The method according to claim 17, wherein the material comprises a disinfectant.

19. The method according to claim 18, wherein the disinfectant is hydrogen peroxide or an alcohol.

20. The method according to claim 19, wherein the secondary vacuum cycle is repeated at least once and the aerosolized material is moved into the treatment chamber at least once when the vacuum cycle is repeated.

\* \* \* \* \*